United States Patent [19]
Holton et al.

[11] Patent Number: 5,994,576
[45] Date of Patent: Nov. 30, 1999

[54] C7 TRICYCLIC TAXANES

[75] Inventors: Robert A. Holton, Tallahassee, Fla.; Ki-byung Chai, Seoul, Rep. of Korea

[73] Assignee: Florida State University, Tallahassee, Fla.

[21] Appl. No.: 08/986,976

[22] Filed: Dec. 8, 1997

Related U.S. Application Data

[62] Division of application No. 08/462,123, Jun. 5, 1995, Pat. No. 5,721,268, which is a continuation of application No. 08/095,160, Jul. 20, 1993, abandoned, which is a continuation-in-part of application No. 08/034,247, Mar. 22, 1993, Pat. No. 5,430,160, which is a continuation-in-part of application No. 07/949,107, Sep. 22, 1992, abandoned, which is a continuation-in-part of application No. 07/863,849, Apr. 6, 1992, abandoned, which is a continuation-in-part of application No. 07/862,955, Apr. 3, 1992, abandoned, which is a continuation-in-part of application No. 07/763,805, Sep. 23, 1991, abandoned.

[51] Int. Cl.$^6$ ................... C07C 271/10; C07D 305/14
[52] U.S. Cl. .................... 560/160; 549/510; 549/511
[58] Field of Search .................... 549/510, 511; 560/160

[56] References Cited

U.S. PATENT DOCUMENTS

| | | | |
|---|---|---|---|
| 4,814,470 | 3/1989 | Colin et al. | 514/499 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 4,960,790 | 10/1990 | Stella et al. | 514/449 |
| 5,015,744 | 5/1991 | Holton | 549/510 |
| 5,136,060 | 8/1992 | Holton | 549/510 |
| 5,175,315 | 12/1992 | Holton | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,254,580 | 10/1993 | Chen et al. | 514/449 |
| 5,254,703 | 10/1993 | Holton | 549/510 |
| 5,264,591 | 11/1993 | Bombardelli et al. | 549/214 |
| 5,272,171 | 12/1993 | Ueda et al. | 514/449 |
| 5,274,124 | 12/1993 | Holton | 549/214 |
| 5,283,253 | 2/1994 | Holton et al. | 514/449 |
| 5,284,864 | 2/1994 | Holton et al. | 514/449 |
| 5,284,865 | 2/1994 | Holton et al. | 549/449 |
| 5,294,637 | 3/1994 | Chen et al. | 514/49 |
| 5,296,506 | 3/1994 | Kingston et al. | 514/449 |
| 5,336,785 | 8/1994 | Holton | 549/214 |
| 5,338,872 | 8/1994 | Holton et al. | 549/510 |
| 5,350,866 | 9/1994 | Holton et al. | 549/510 |
| 5,352,806 | 10/1994 | Gunawardana et al. | 549/510 |
| 5,384,399 | 1/1995 | Holton | 544/97 |
| 5,399,726 | 3/1995 | Holton et al. | 549/510 |
| 5,405,972 | 4/1995 | Holton et al. | 549/214 |
| 5,430,160 | 7/1995 | Holton | 549/510 |
| 5,440,056 | 8/1995 | Klein et al. | 549/510 |
| 5,466,834 | 11/1995 | Holton | 549/510 |
| 5,478,854 | 12/1995 | Farina et al. | 514/374 |
| 5,489,601 | 2/1996 | Holton et al. | 514/337 |
| 5,530,020 | 6/1996 | Gunawardana et al. | 514/449 |
| 5,532,363 | 7/1996 | Holton | 544/97 |
| 5,539,103 | 7/1996 | Holton | 540/354 |
| 5,594,157 | 1/1997 | Gunawardana et al. | 549/510 |
| 5,616,740 | 4/1997 | Klein et al. | 549/510 |
| 5,721,268 | 2/1998 | Holton et al. | 514/449 |

FOREIGN PATENT DOCUMENTS

| | | |
|---|---|---|
| 0400971 A2 | 12/1990 | European Pat. Off. . |
| 0428376 A1 | 5/1991 | European Pat. Off. . |
| 0534707 A1 | 9/1992 | European Pat. Off. . |
| 0534708 A1 | 9/1992 | European Pat. Off. . |
| 0534709 A1 | 9/1992 | European Pat. Off. . |
| 919224 | 11/1993 | South Africa . |
| WO 93/02065 | 3/1993 | WIPO . |
| WO 93/21173 | 10/1993 | WIPO . |
| WO 94/17050 | 8/1994 | WIPO . |

OTHER PUBLICATIONS

S. Borman, "New Family of Taxol, Taxotere Analogs Developed" Science & Technology, Chem. & Eng. News, pp. 26–27, (Apr. 1993).

V. Farina et al., "The Chemistry of Taxanes: Unexpected Rearrangement Of Baccatin III During Chemoselective Debenzoylation with Bu$_3$SnOMe/LiCl", *Tetrahedron Letters, vol. 33*, No. 28, pp. 3979–3982 (1992).

D. Kingston et al., "The Chemistry of Taxol, A Clinically Useful Anticancer Agent", Journal of Natural Products, vol. 53, No. 1 (1990) pp. 1–12.

Kingston et al., "Progress in the Chemistry of Organic Natural Products 61", Springer–Verlag, Wien New York 1993.

N. Magri et al., "Modified Taxols, 4. Synthesis and Biological Activity of Taxols Modified in the Side Chain", J. of Natural Products, vol. 51, No. 2 (1988) pp. 298–306.

W. Mellado et al., "Preparation and Biological Activity of Taxol Acetates", Biochem. & Biophys. Research Communications, vol. 124, No. 2 (1984) pp. 329–336.

Ojima et al., "New and Efficient Approaches to the Semisynthesis of Taxol and Its C–13 Side Chain Analogs by Means of β–Lactam Synthon Method", Tetrahedron Letters, vol. 48, No. 34, pp. 6985–7012 (1992).

G. Samaranayake et al., "Modified Taxols, 5. Reaction of Taxol With Electrophilic Reagents and Preparation of a Rearranged Taxol Derivative with Tubulin Assembly Activity", J. Org. Chem., vol. 56 (1991) pp. 5114–5119.

*Primary Examiner*—Ba K. Trinh
*Attorney, Agent, or Firm*—Senniger, Powers, Leavitt & Roedel

[57] ABSTRACT

Taxane derivatives having alternative C7 substituents.

28 Claims, No Drawings

C7 TRICYCLIC TAXANES

REFERENCE TO RELATED APPLICATIONS

"This application is a divisional application of U.S. Ser. No. 08/462,123, filed Jun. 5, 1995, now U.S. Pat. No. 5,721,268 which is a file wrapper continuation application of U.S. Ser. No. 08/095,160, filed Jul. 20, 1993, now abandoned which is a continuation-in-part application of U.S. Ser. No. 08/034,247 filed Mar. 22, 1993, now U.S. Pat. No. 5,430,160, which is a continuation-in-part application of U.S. Ser. No. 07/949,107, filed Sep. 22, 1992, now abandoned which is a continuation-in-part application of U.S. Ser. No. 07/863,849, filed Apr. 6, 1992, now abandoned, which is a continuation-in-part application of U.S. Ser. No. 07/862,955, filed Apr. 3, 1992, now abandoned, which is a continuation-in-part application of U.S. Ser. No. 07/763,805, filed Sep. 23, 1991, now abandoned."

This invention was made with Government support under NIH Grant #CA 42031 and NIH Grant #CA 55131 awarded by the National Institutes of Health. The Government has certain rights in the invention.

BACKGROUND OF THE INVENTION

The present invention is directed to novel taxanes which have utility as antileukemia and antitumor agents.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has a 2'R, 3'S configuration and the following structural formula:

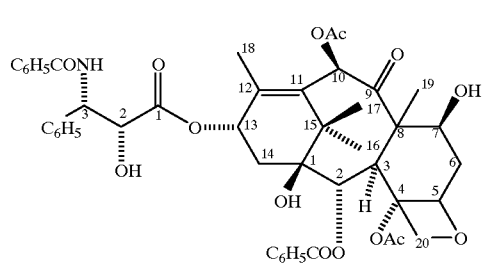

(1)

wherein Ac is acetyl. Because of this promising activity, taxol is currently undergoing clinical trials in both France and the United States.

Colin et al. reported in U.S. Pat. No. 4,814,470 that taxol derivatives having structural formula (2) below, have an activity significantly greater than that of taxol (1).

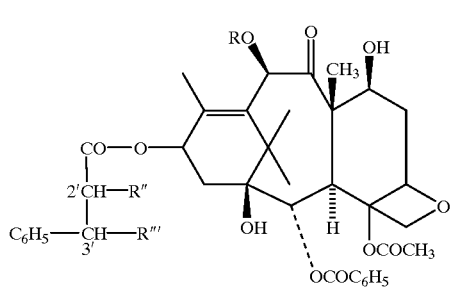

(2)

R' represents hydrogen or acetyl and one of R" and R'" represents hydroxy and the other represents tert-butoxycarbonylamino and their stereoisomeric forms, and mixtures thereof. The compound of formula (2) in which R' is hydrogen R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxane derivatives which are valuable antileukemia and antitumor agents.

Briefly, therefore, the present invention is directed to C7 taxane derivatives. In a preferred embodiment, the taxane derivative has a tricyclic or tetracyclic core and corresponds to the formula:

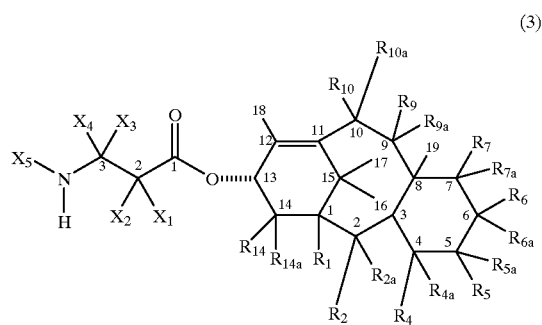

(3)

wherein $X_1$ is $-OX_6$, $-SX_7$, or $-NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is $-COX_{10}$, $-COOX_{10}$, $-COSX_{10}$, $-CONX_8X_{10}$, or $-SO_2X_{11}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, $-OX_{10}$, or $-NX_8X_{14}$;

$X_{14}$ is hydrogen, alkyl, alkenyl, alkynyl, aryl, or heteroaryl;

$R_1$ is hydrogen, hydroxy, protected hydroxy or together with $R_{14}$ forms a carbonate;

$R_2$ is hydrogen, hydroxy, $-OCOR_{31}$, or together with $R_{2a}$ forms an oxo;

$R_{2a}$ is hydrogen or together with $R_2$ forms an oxo;

$R_4$ is hydrogen, together with $R_{4a}$ forms an oxo, oxirane or methylene, or together with $R_{5a}$ and the carbon atoms to which they are attached form an oxetane ring;

$R_{4a}$ is hydrogen, alkyl, alkenyl, alkynyl, aryl, heteroaryl, cyano, hydroxy, —OCOR$_{30}$, or together with R$_4$ forms an oxo, oxirane or methylene;

$R_5$ is hydrogen or together with $R_{5a}$ forms an oxo, $R_{5a}$ is hydrogen, hydroxy, protected hydroxy, acyloxy, together with R$_5$ forms an oxo, or together with R$_4$ and the carbon atoms to which they are attached form an oxetane ring;

R$_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with R$_6$ forms an oxo;

R$_7$ is hydrogen or acyloxy;

$R_{7a}$ is hydrogen;

R$_9$ is hydrogen or together with $R_{9a}$ forms an oxo;

$R_{9a}$ is hydrogen, hydroxy, protected hydroxy, acyloxy, or together with R$_9$ forms an oxo;

$R_{10}$ is hydrogen or together with $R_{10a}$ forms an oxo;

$R_{10a}$ is hydrogen or together with $R_{10}$ forms an oxo;

$R_{14}$ is hydrogen, alkyl, alkenyl, alkynyl, aryl, or heteroaryl, hydroxy, protected hydroxy or together with R$_1$ forms a carbonate;

$R_{14a}$ is hydrogen, alkyl, alkenyl, alkynyl, aryl, or heteroaryl;

$R_{28}$ is hydrogen, acyl, hydroxy protecting group or a functional group which increases the solubility of the taxane derivative; and $R_{29}$, $R_{30}$ and $R_{31}$ are independently hydrogen, alkyl, alkenyl, alkynyl, monocyclic aryl or monocyclic heteroaryl.

Other objects and features of this invention will be in part apparent and in part pointed out hereinafter.

DETAILED DESCRIPTION OF THE PREFERRED EMBODIMENTS

As used herein "Ar" means aryl; "Ph" means phenyl; "Ac" means acetyl; "Et" means ethyl; "R" means alkyl unless otherwise defined; "Bu" means butyl; "Pr" means propyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LHMDS" means lithium hexamethyldisilazide; "LAH" means lithium aluminum hydride; "Red-Al" means sodium bis(2-methoxyethoxy) aluminum hydride; "AIBN" means azo-(bis)-isobutyronitrile; "10-DAB" means 10-desacetylbaccatin III; FAR means 2-chloro-1,1,2-trifluorotriethylamine; protected hydroxy means —OR wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined herein are preferably lower alkyl containing from one to six carbon atoms in the principal chain and up to 15 carbon atoms. They may be substituted, straight, branched chain or cyclic and include methyl, ethyl, propyl, isopropyl, butyl, hexyl, cyclopropyl, cyclopentyl, cyclohexyl and the like.

The alkenyl groups described herein, either alone or with the various substituents defined herein are preferably lower alkenyl containing from two to six carbon atoms in the principal chain and up to 15 carbon atoms. They may be substituted, straight or branched chain and include ethenyl, propenyl, isopropenyl, butenyl, isobutenyl, hexenyl, and the like.

The alkynyl groups described herein, either alone or with the various substituents defined herein are preferably lower alkynyl containing from two to six carbon atoms in the principal chain and up to 15 carbon atoms. They may be substituted, straight or branched chain and include ethynyl, propynyl, butynyl, isobutynyl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, and amido.

The acyloxy groups described herein contain alkyl, alkenyl, alkynyl, aryl or heteroaryl groups.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

In accordance with the present invention, it has been discovered that compounds corresponding to structural formula 3 show remarkable properties, in vitro, and are valuable antileukemia and antitumor agents. Their biological activity has been determined in vitro, using tubulin assays according to the method of Parness et al., *J. Cell Biology*, 91: 479–487 (1981) and human cancer cell lines, and is comparable to that exhibited by taxol and taxotere.

In a preferred embodiment of the present invention, the taxane has a structure corresponding to taxol or taxotere except for the C7 substituents ($R_{7a}$ being hydrogen and R$_7$ being hydrogen or acyloxy). That is, $R_{2a}$ is hydrogen, R$_2$ is benzoyloxy, $R_{14}$ and $R_{14a}$ are hydrogen, $R_9$ and $R_{9a}$ form an oxo, $R_{10a}$ is hydrogen, $R_{10}$ is hydroxy or acetoxy, $R_5$ is hydrogen, $R_{5a}$ and $R_4$ and the carbons to which they are attached form an oxetane ring, $R_{4a}$ is acetoxy, $R_1$ is hydroxy, $X_1$ is —OH, $X_2$ is hydrogen, $X_3$ is phenyl, $X_4$ is hydrogen, $X_5$ is —COX$_{10}$, and $X_{10}$ is phenyl or t-butoxy and the taxane has the 2'R, 3'S configuration.

In other embodiments of the present invention, the taxane has a structure which differs from that of taxol or taxotere with respect to the C7 substituent and at least one other substituent. For example, $R_2$ may be hydroxy or —OCOR$_{31}$ wherein $R_{31}$ is hydrogen, alkyl or selected from the group comprising

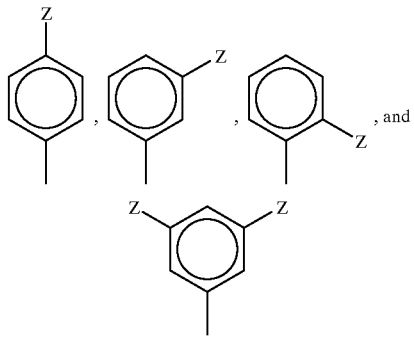

and Z is alkyl, hydroxy, alkoxy, halogen, or trifluoromethyl. $R_{9a}$ may be hydrogen and $R_9$ may be hydrogen or hydroxy, $R_{10a}$ may be hydrogen and $R_{10}$ may be acetoxy or other acyloxy or $R_{10}$ and $R_{10a}$ may be oxo, $X_3$ may be selected from isobutenyl, isopropyl, cyclopropyl, n-butyl, t-butyl, cyclobutyl, amyl cyclohexyl, furyl, thienyl, pyridyl or the substituted derivatives thereof, $X_5$ may be —COX$_{10}$ or —COOX$_{10}$ and $X_{10}$ may be selected from furyl, thienyl, alkyl substituted furyl or thienyl, pyridyl, tert-, iso- or n-butyl, ethyl, iso- or n-propyl, cyclopropyl, cyclohexyl, allyl, crotyl, 1,3-diethoxy-2-propyl, 2-methoxyethyl, amyl, neopentyl, PhCH$_2$O—, —NPh$_2$, —NHnPr, —NHPh, and —NHEt.

Taxanes having the general formula 3 may be obtained by reacting a β-lactam with alkoxides having the taxane tricyclic or tetracyclic nucleus and a C-13 metallic oxide substituent to form compounds having a β-amido ester substituent at C-13. The β-lactams have the following structural formula:

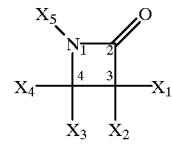

wherein $X_1$–$X_5$ are as defined above.

The β-lactams can be prepared from readily available materials, as is illustrated in schemes A and B below:

Scheme A

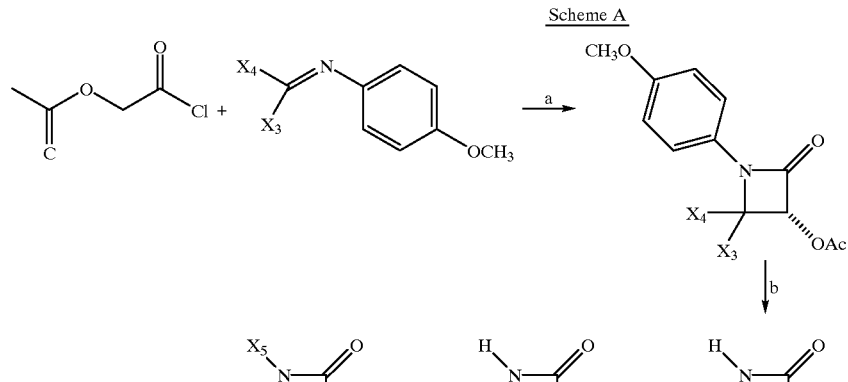

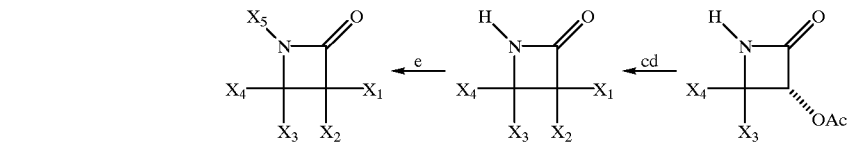

Scheme B

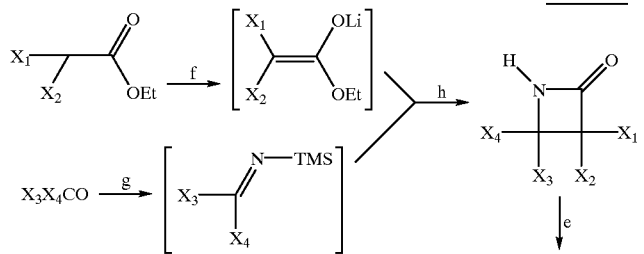

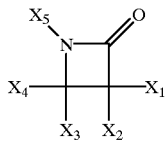

reagents: (a) triethylamine, $CH_2Cl_2$, 25° C., 18 h; (b) 4 equiv ceric ammonium nitrate, $CH_3CN$, −10° C., 10 min; (c) KOH, THF, $H_2O$, 0° C., 30 min, or pyrolidine, pyridine, 25° C., 3 h, (d) TESCl, pyridine, 25° C., 30 min or 2-methoxypropene toluene sulfonic acid (cat.), THF, 0° C., 2 h; (e) n-butyllithium, THF, −78° C., 30 min; and an acyl chloride or chloroformate ($X_5$=—$COX_{10}$), sulfonyl chloride ($X_5$=—$COSX_{10}$) or isocyanate ($X_5$=—$CONX_8X_{10}$); (f) lithium diisopropyl amide, THF −78° C. to −50° C.; (g) lithium hexamethyldisilazide, THF −78° C. to 0° C.; (h) THF, −78° C. to 25° C., 12 h.

The starting materials are readily available. In scheme A, α-acetoxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones. The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones. In Scheme B, ethyl-α-triethylsilyloxyacetate is readily prepared from glycolic acid.

In Schemes A and B, $X_1$ is preferably —$OX_6$ and $X_6$ is a hydroxy protecting group. Protecting groups such as 2-methoxypropyl ("MOP"), 1-ethoxyethyl ("EE") are preferred, but a variety of other standard protecting groups such as the triethylsilyl group or other trialkyl (or aryl) silyl groups may be used. As noted above, additional hydroxy protecting groups and the synthesis thereof may be found in "Protective groups in Organic Synthesis" by T. W. Greene, John Wiley & Sons, 1981.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached has the advantage of being highly diastereoselective, thus permitting the use of a racemic mixture of side chain precursor.

The alkoxides having the tricyclic or tetracyclic taxane nucleus and a C-13 metallic oxide or ammonium oxide substituent have the following structural formula:

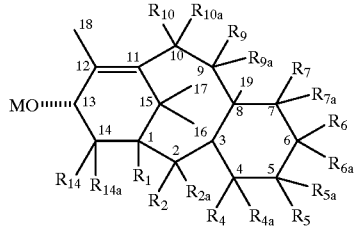

wherein $R_1$–$R_{14a}$ are as previously defined and M comprises ammonium or is a metal optionally selected from the group comprising Group IA, Group IIA and transition metals, and preferably, Li, Mg, Na, K or Ti. Most preferably, the alkoxide has the tetracyclic taxane nucleus and corresponds to the structural formula:

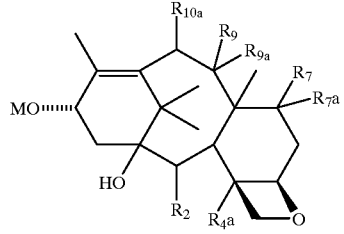

wherein M, $R_2$, $R_{4a}$, $R_7$, $R_{7a}$, $R_9$, $R_{9a}$, $R_{10}$, and $R_{10a}$ are as previously defined.

The alkoxides can be prepared by reacting an alcohol having the taxane nucleus and a C-13 hydroxyl group with an organometallic compound in a suitable solvent. Most preferably, the alcohol is a protected baccatin III, in particular, 7-O-triethylsilyl baccatin III (which can be obtained as described by Greene, et al. in JACS 110: 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

(4)

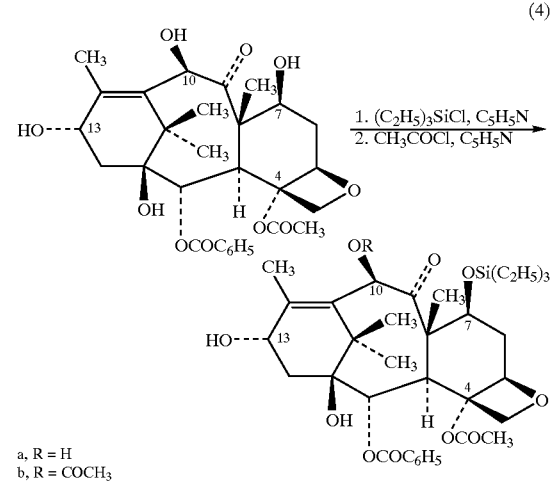

a, R = H
b, R = $COCH_3$

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (4a) as a reaction product in 84–86% yield after purification. The reaction product may then optionally be acetylated with 5 equivalents of $CH_3COCl$ and 25 mL of pyridine/mmol of 4a at 0° C. under an argon atmosphere for 48 hours to provide 86% yield of 7-O-triethylsilyl baccatin III (4b). Greene, et al. in JACS 110, 5917 at 5918 (1988).

The 7-protected baccatin III (4b) is reacted with an organometallic compound such as LHMDS in a solvent such as tetrahydrofuran (THF), to form the metal alkoxide 13-O-lithium-7-O-triethylsilyl baccatin III as shown in the following reaction scheme:

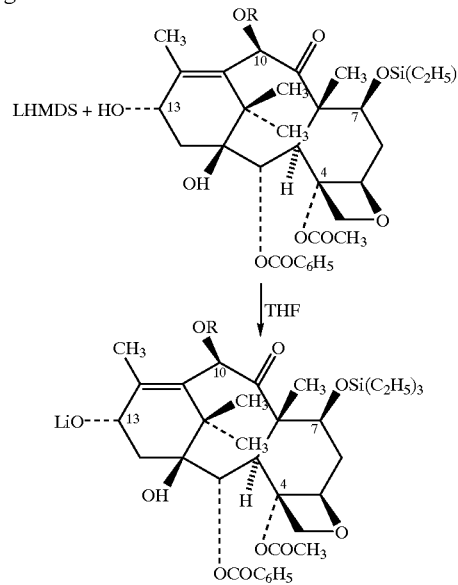

As shown in the following reaction scheme, 13-O-lithium-7-O-triethylsilyl baccatin III reacts with a β-lactam in which $X_1$ is preferably —$OX_6$, ($X_6$ being a hydroxy protecting group) and $X_2$–$X_5$ are as previously defined to provide an intermediate in which the C-7 and C-2' hydroxyl groups are protected. The protecting groups are then hydrolyzed under mild conditions so as not to disturb the ester linkage or the taxane substituents.

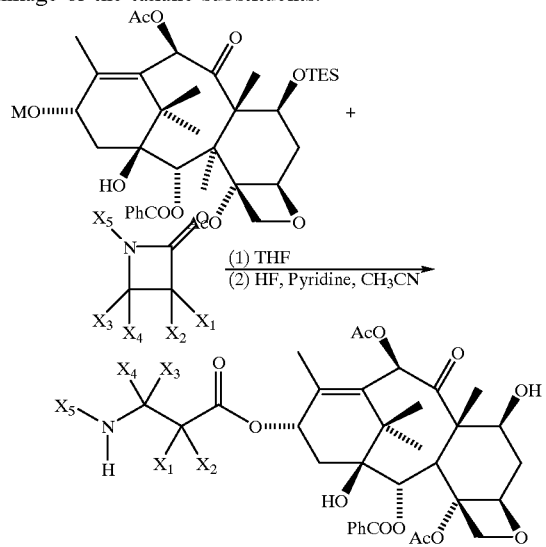

Both the conversion of the alcohol to the alkoxide and the ultimate synthesis of the taxane derivative can take place in the same reaction vessel. Preferably, the β-lactam is added to the reaction vessel after formation therein of the alkoxide.

Compounds of formula 3 of the instant invention are useful for inhibiting tumor growth in animals including humans and are preferably administered in the form of a pharmaceutical composition comprising an effective antitumor amount of compound of the instant invention in combination with a pharmaceutically acceptable carrier or diluent.

Antitumor compositions herein may be made up in any suitable form appropriate for desired use; e.g., oral, parenteral or topical administration. Examples of parenteral administration are intramuscular, intravenous, intraperitoneal, rectal and subcutaneous administration.

The diluent or carrier ingredients should not be such as to diminish the therapeutic effects of the antitumor compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions and the like. They may also be manufactured in the form of sterile solid compositions which can be dissolved or suspended in sterile injectable medium immediately before use. They may contain suspending or dispersing agents known in the art.

The water solubility of compounds of formula (3) may be improved by modification of the C2' and/or C7 substituents. For instance, water solubility may be increased if $X_1$ is —$OX_6$ and $R_{7a}$ is —$OR_{28}$, and $X_6$ and $R_{28}$ are independently hydrogen or —$COGCOR^1$ wherein G is ethylene, propylene, —CH=CH—, 1,2-cyclohexane, or 1,2-phenylene, $R^1$=OH base, $NR^2R^3$, $OR^3$, $SR^3$, $OCH_2CONR^4R^5$, OH $R^2$=hydrogen, methyl $R^3$=$(CH_2)_n NR^6R^7$; $(CH_2)_n N^{\oplus} R^6R^7R^8 X^{\ominus}$ n=1 to 3

$R^4$=hydrogen, lower alkyl containing 1 to 4 carbons $R^5$=hydrogen, lower alkyl containing 1 to 4 carbons, benzyl, hydroxyethyl, $CH_2CO_2H$, dimethylaminoethyl $R^6R^7$=lower alkyl containing 1 or 2 carbons, benzyl or $R^6$ and $R^7$ together with the nitrogen atom of $NR^6R^7$ form the following rings

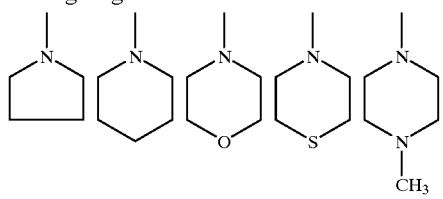

$R^8$=lower alkyl containing 1 or 2 carbons, benzyl $X^{\ominus}$=halide base=$NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $X_1$ or $X_2$ is —$COGCOR^1$ is set forth in Haugwitz U.S. Pat. No. 4,942,184 which is incorporated herein by reference.

Alternatively, solubility may be increased when $X_1$ is —$OX_6$ and $X_6$ is a radical having the formula —COCX=CHX or —COX—CHX—CHX—$SO_2O$—M wherein X is hydrogen, alkyl or aryl and M is hydrogen, alkaline metal or an ammonio group as described in Kingston et al., U.S. Pat. No. 5,059,699 (incorporated herein by reference).

Taxanes having alternative C9 substituents may be prepared by selectively reducing the C9 keto substituents to yield the corresponding C9 β-hydroxy derivative. The reducing agent is preferably a borohydride and, most preferably, tetrabutylammoniumborohydride ($Bu_4NBH_4$) or triacetoxyborohydride.

As illustrated in Reaction Scheme 1, the reaction of baccatin III with $Bu_4NBH_4$ in methylene chloride yields 9-desoxo-9β-hydroxybaccatin III 5. After the C7 hydroxy group is protected with the triethylsilyl protecting group, for example, a suitable side chain may be attached to 7-protected-9β-hydroxy derivative 6 as elsewhere described herein. Removal of the remaining protecting groups thus yields 9β-hydroxy-desoxo taxol or other 9β-hydroxytetracylic taxane having a C13 side chain.

REACTION SCHEME 1

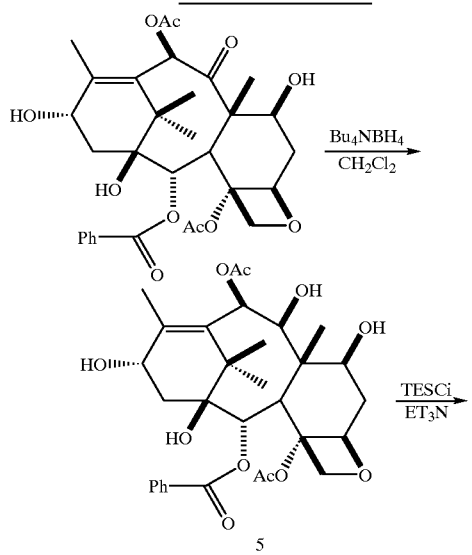

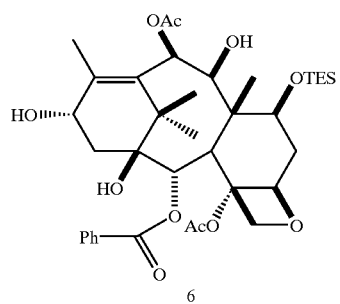

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

REACTION SCHEME 2

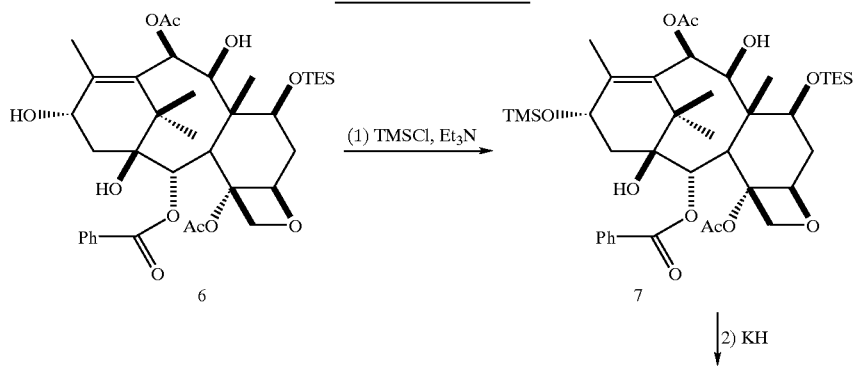

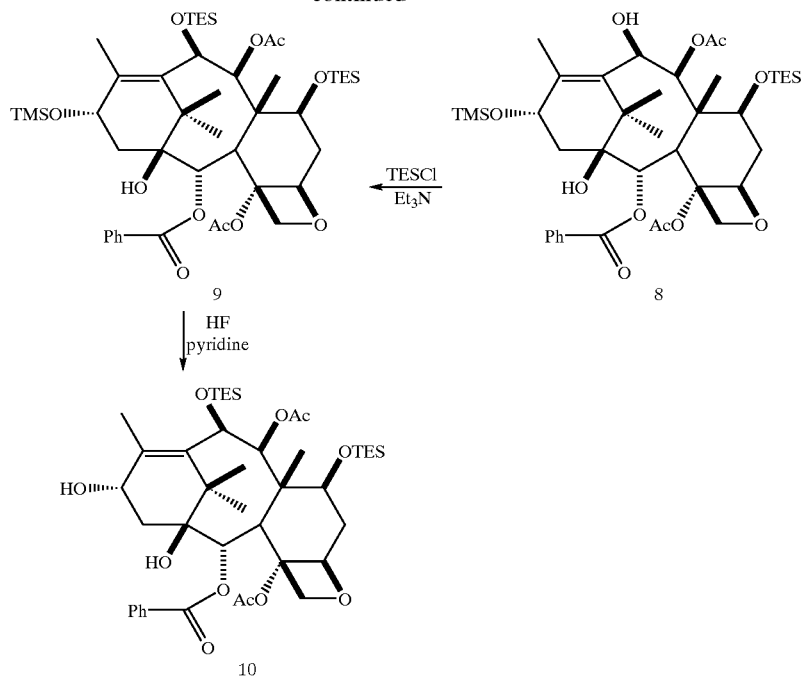

As shown in Reaction Scheme 3, 10-oxo derivative 11 can be provided by oxidation of lo-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a C13 side chain.

REACTION SCHEME 3

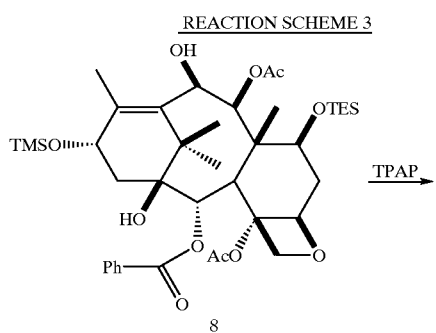

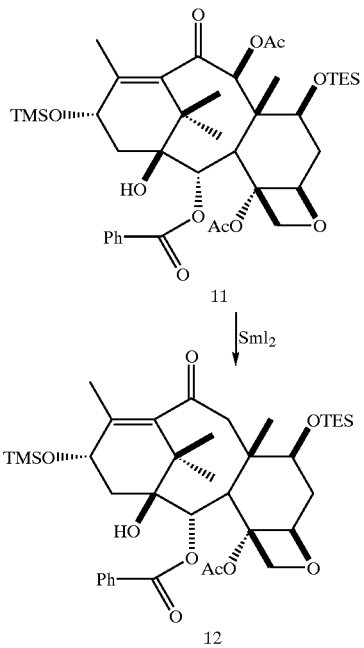

Reaction Scheme 4 illustrates a reaction in which 10-DAB is reduced to yield pentaol 13. The C7 and C10 hydroxyl groups of pentaol 13 can then be selectively protected with the triethylsilyl or another protecting group to produce triol 14 to which a C13 side chain can be attached as described above or, alternatively, after further modification of the tetracylic substituents.

REACTION SCHEME 4

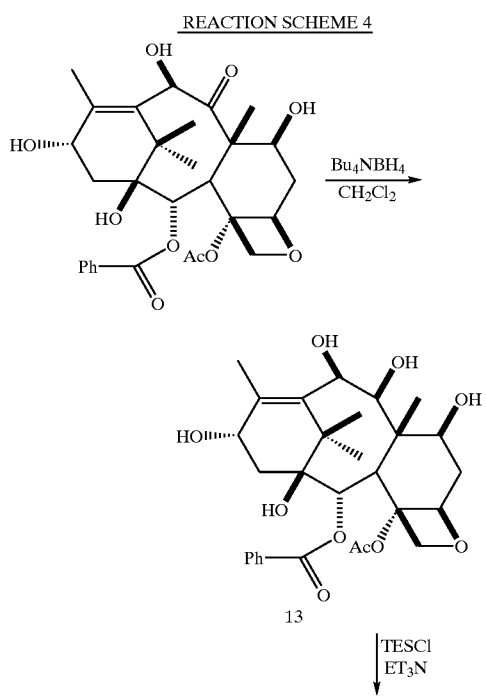

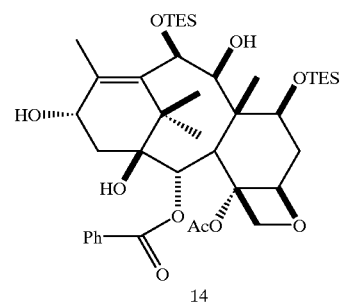

Taxanes having C9 and/or C10 acyloxy substituents other than acetate can be prepared using 10-DAB as a starting material as illustrated in Reaction Scheme 5. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached. Alternatively, the C10 and C9 groups can be caused to migrate as set forth in Reaction Scheme 2, above.

REACTION SCHEME 5

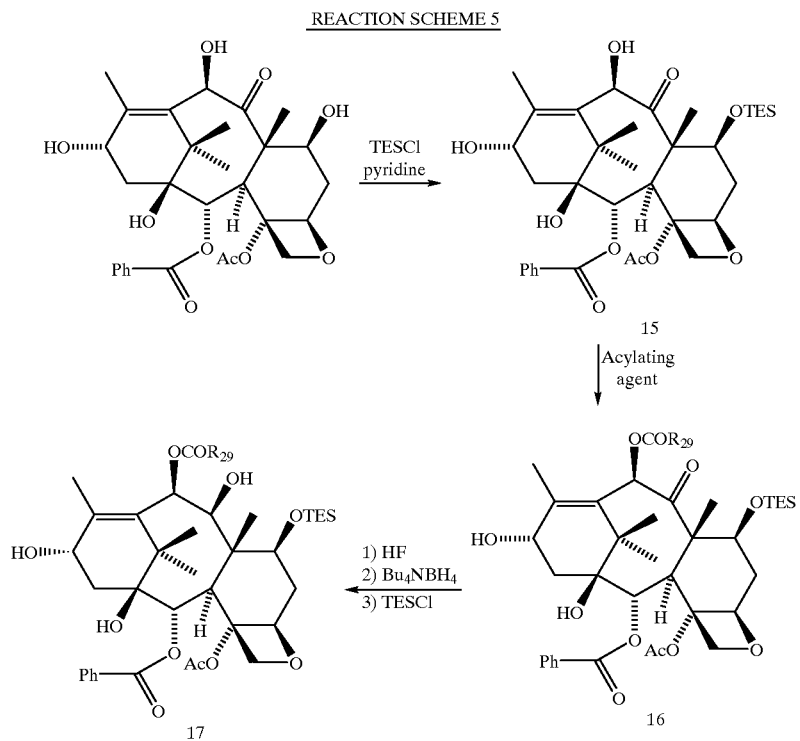

Taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. Derivatives of the baccatin III and 10-DAB analogs having different substituents at C10 and at least one other position, for instance C1, C2, C4, C7, C9 and C13, can then be prepared by carrying out any of the other reactions described herein and any others which are within the level of skill in the art.

In Reaction Scheme 6, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

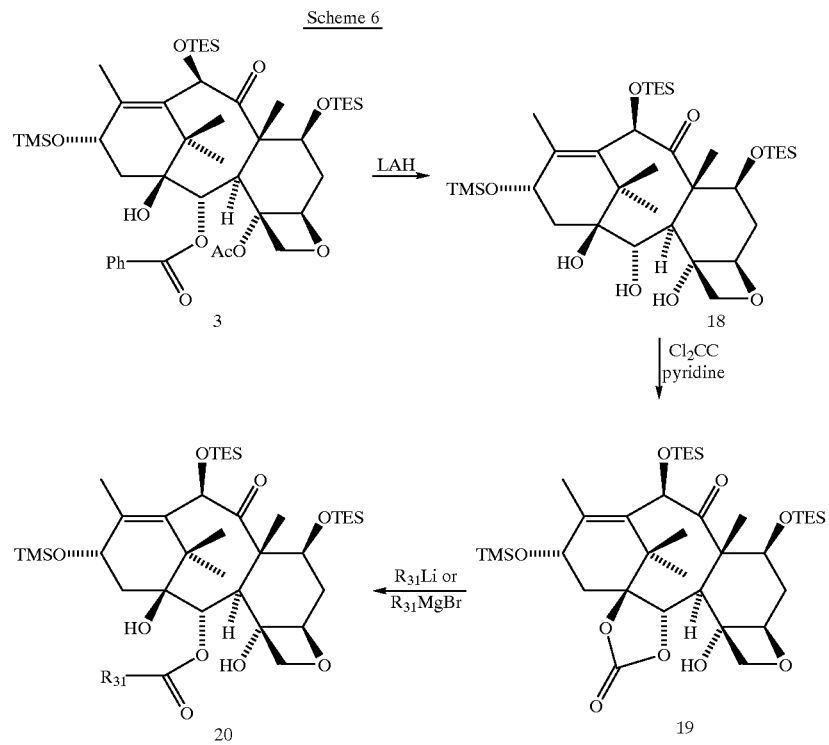

Scheme 6

Deprotonation of triol 18 with LDA followed by introduction of an acid chloride selectively gives the C4 ester. For example, when acetyl chloride was used, triol 18 was converted to 1,2 diol 4 as set forth in Reaction Scheme 7. Triol 18 can also readily be converted to the 1,2 carbonate 19. Acetylation of carbonate 19 under vigorous standard conditions provides carbonate 21 as described in Reaction Scheme 8; addition of alkyllithiums or Grignard reagents to carbonate 19 provides the C2 ester having a free hydroxyl group at C4 as set forth in Reaction Scheme 6.

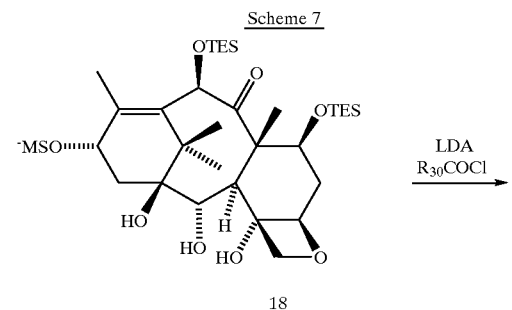

Scheme 7

-continued

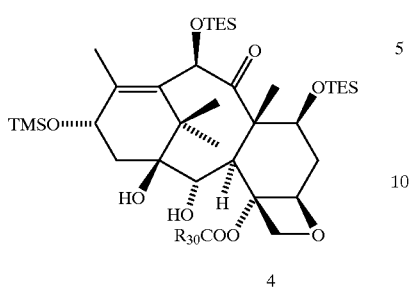
4

Scheme 8

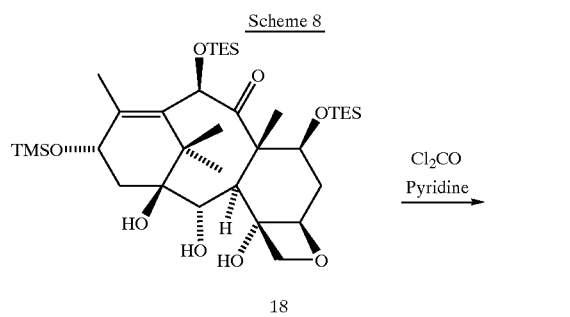

-continued

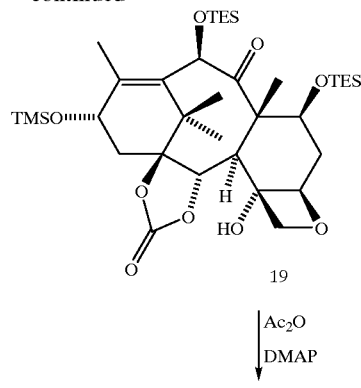
19

| Ac₂O
↓ DMAP

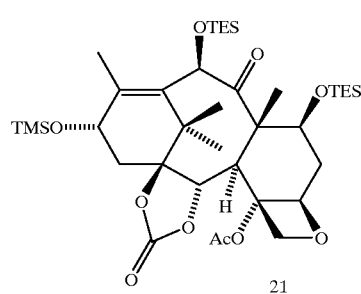
21

As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.

Scheme 9

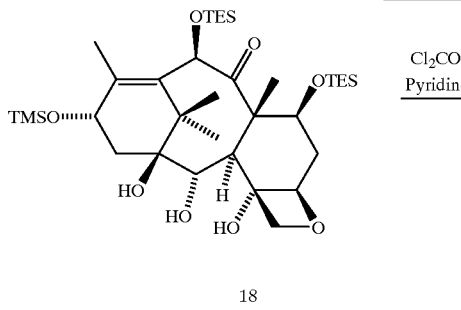
18

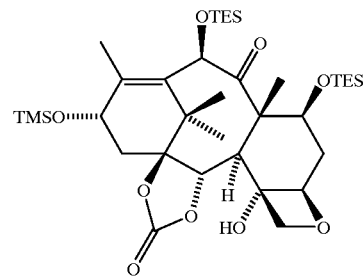
19

| R₃₀COCl
pyridine
↓ DMAP

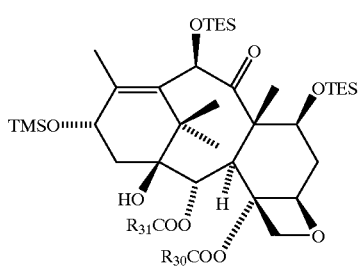
23

← R₃₁Li or R₃₁MgBr

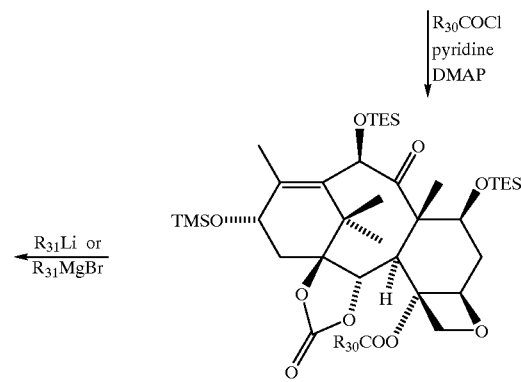
22

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10.

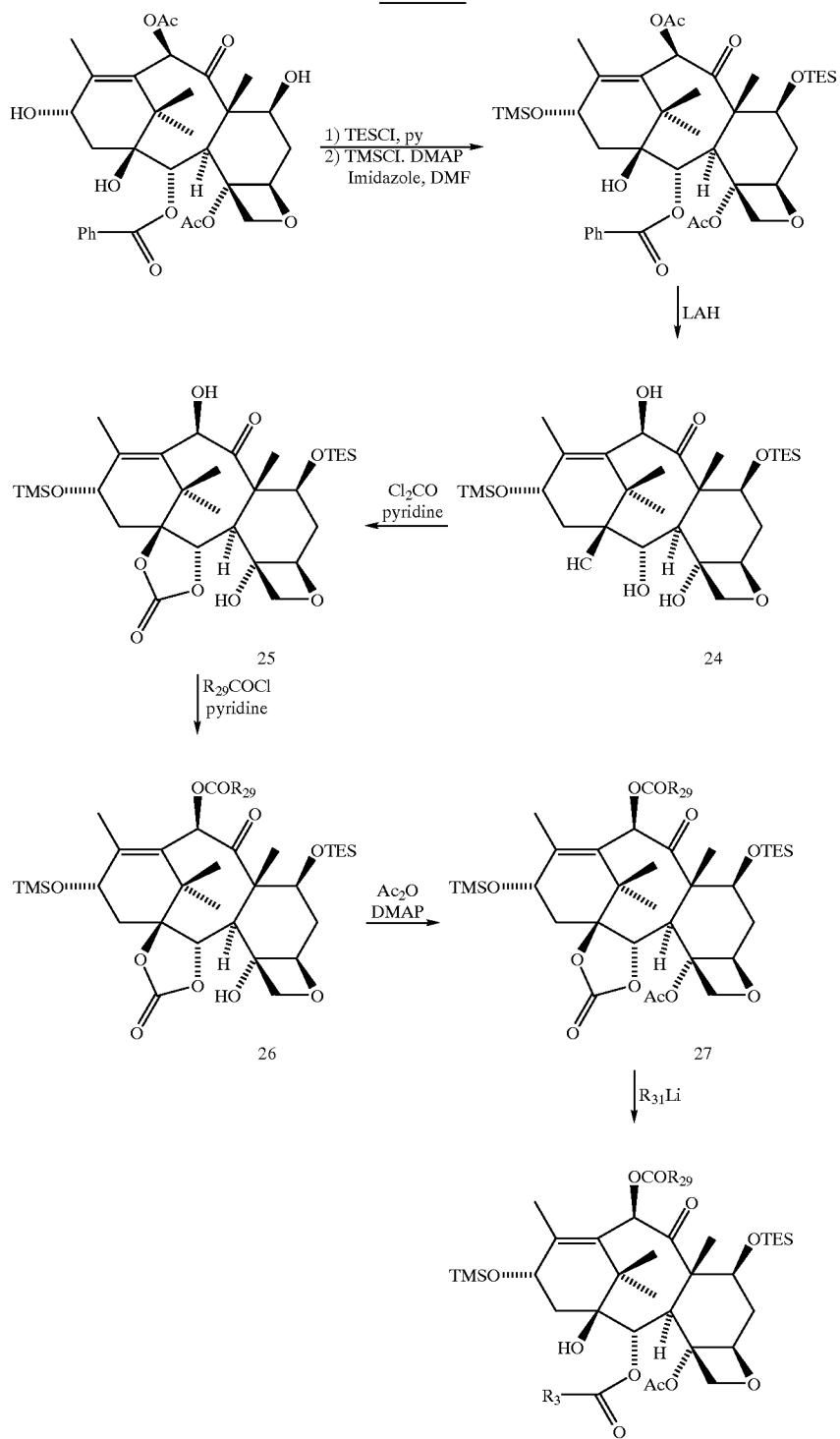

Scheme 10

10-desacetoxy derivatives of baccatin III and 10-desoxy derivatives of 10-DAB may be prepared by reacting baccatin III or 10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed. Thereafter, the C9 keto substituent may be reduced to provide the corresponding 9-desoxo-9β-hydroxy-10-desacetyoxy or 10-desoxy derivatives as otherwise described herein.

C7 dihydro substituted taxanes can be prepared as set forth in Reaction Schemes 11 and 12.

REACTION SCHEME 11

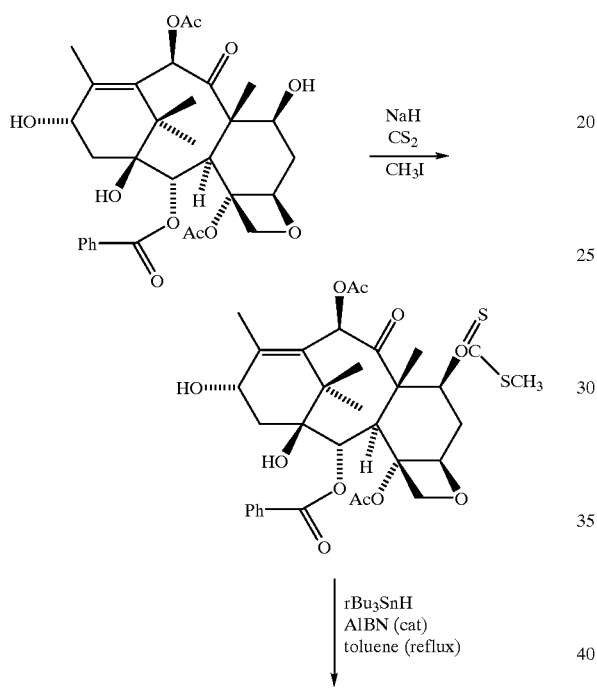

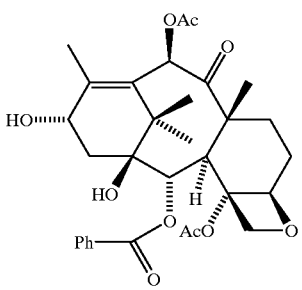

Taxanes having C7 acyloxy substituents can be prepared as set forth in Reaction Scheme 12, 7,13-protected 10-oxo-derivative 11 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

REACTION SCHEME 12

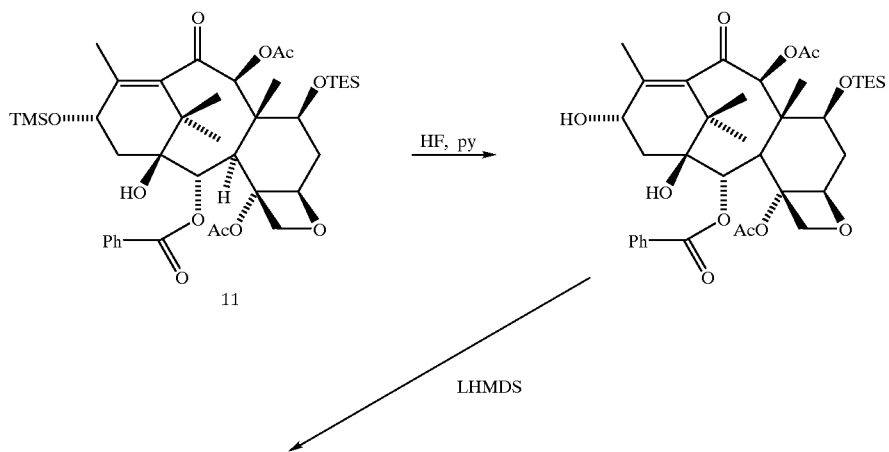

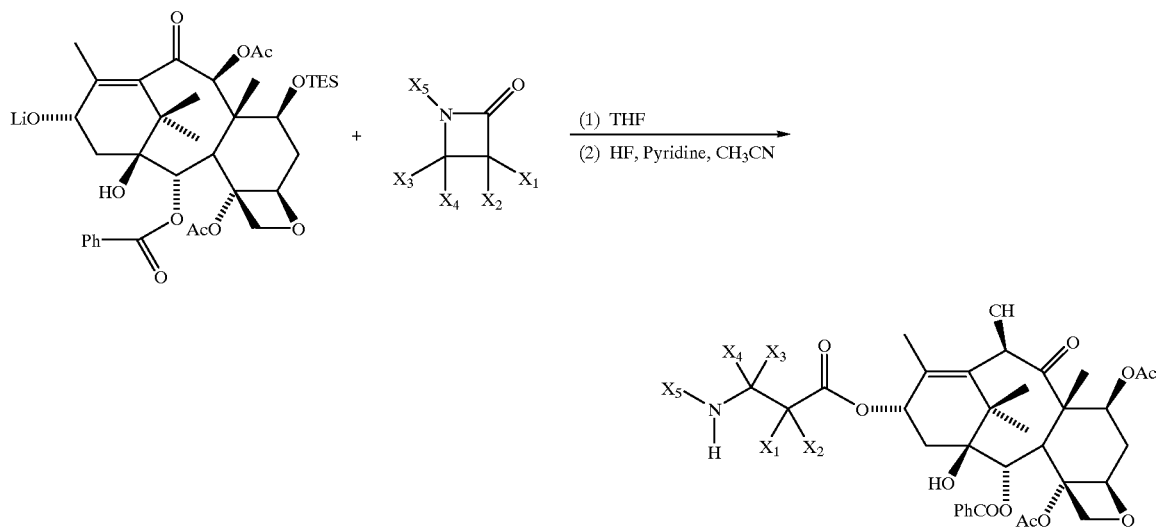

A wide variety of tricyclic taxanes are naturally occurring, and through manipulations analogous to those described herein, an appropriate side chain can be attached to the C13 oxygen of these substances. Alternatively, as shown in Reaction Scheme 13, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

REACTION SCHEME 13

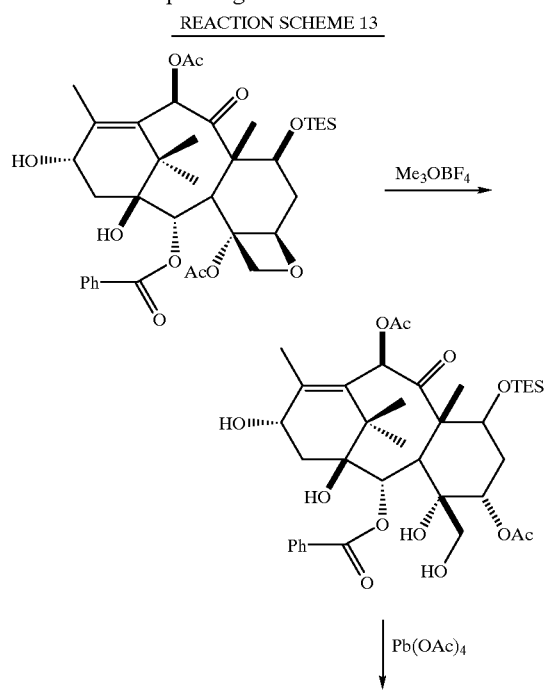

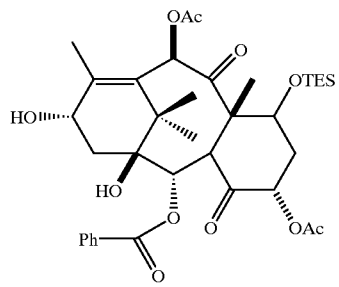

Recently a hydroxylated taxane (14-hydroxy-10-deacetylbaccatin III) has been discovered in an extract of yew needles (C&EN, p 36–37, Apr. 12, 1993). Derivatives of this hydroxylated taxane having the various C2, C4, etc. functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C7, C9, C10 and C13 substituents.

The following examples are provided to more fully illustrate the invention.

EXAMPLE 1

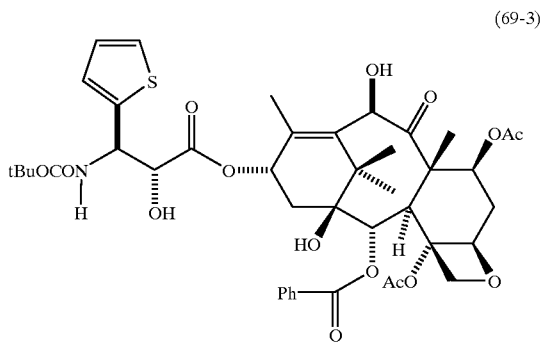

(69-3)

Preparation of 3'-desphenyl-3'-(2-thienyl)-N-desbenzoyl-N-(t-butoxycarbonyl)-7-O-acetyl-10-desacetyl taxol.

To a solution of 7-O-triethylsilyl-9-desoxy-9β-acetoxy-10-desacetoxy-10-keto baccatin (III) (33.2 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (54.2 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 46.5 mg of a mixture containing (2'R,3'S)-2',7-(bis)-O-triethylsilyl-3'-desphenyl-3'-(2-thienyl)-N-desbenzoyl-N-(t-buthoxycarbonyl)-9-desoxy-9β-acetoxy-10-desacetoxy-10-keto taxol and a small amount of the (2'S,3'R) isomer.

To a solution of 46.5 mg (0.043 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.7 mg of material which was purified by flash chromatography to give 22.2 mg (61%) of 3'-desphenyl-3'-(2-thienyl)-N-desbenzoyl-N-(t-butoxycarbonyl)-7-O-acetyl-10-desacetyl taxol, which was recrystallized from methanol/water.

m.p.140.5–143° C.; $[\alpha]^{25}_{Na}$−58.6° (c 0.00245, CHCl$_3$).

$^1$H NMR (CDCl$_3$, 300 MHz) δ 8.11(d, J=6.9 Hz, 2H, benzoate ortho), 7.62(m, 1H, benzoate para), 7.51(m, 2H, benzoate meta), 7.29(dd, J=5.5, 1.4 Hz, 1H, thienyl), 7.09(d, J=3.2 Hz, 1H, thienyl), 7.01(dd, J=3.7, 1.4 Hz, 1H, thienyl), 6.22(dd, J=8.3, 0.9 Hz, 1H, H13), 5.68(d, J=6.9 Hz, 1H, H2), 5.51(d, J=8.7 Hz, H7), 5.45(dd, J=10.5, 7.3 Hz, 1H, H3'), 5.33(d, J=9.2 Hz, 1H, NH), 5.32(s, 1H, H10), 4.93 (dd, J=9.6 1.8 Hz, 1H, H5), 4.64(s, 1H, H2'), 4.33(d, J=8.7 Hz, 1H, H20α), 4.23(d, J=8.7 Hz, 1H, H20β), 4.01(d, J=1.8 Hz, 1H, 10 OH), 4.00(d, J=6.9 Hz, 1H, H3), 3.46(m, 1H, 2'OH), 2.54(m, 1H, H6α), 2.39(s, 3H, 4Ac), 2.33(m, 2H, H14α), 2.01(m, 1H, H14β), 1.99(s, 3H, 7 Ac), 1.92(br s, 3H, Me18), 1.90(m, 1H, H6β), 1.70(s, 3H, Me19), 1.53(s, 1H, 1 OH), 1.35(s, 9H, 3Me t-buthoxy) 1.23(s, 3H, Me17), 1.10(s, 3H, Me16).

EXAMPLE 2

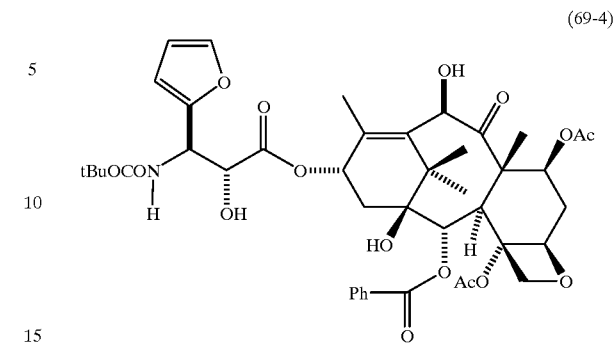

(69-4)

Preparation of 3'-desphenyl-3'-(2-furyl)-N-desbenzoyl-N-(t-butoxycarbonyl)-7-O-acetyl-10-desacetyl taxol.

To a solution of 7-O-triethylsilyl-9-desoxy-9β-acetoxy-10-desacetoxy-10-keto baccatin (III) (33.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)azetidin-2-one (52.0 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 42.1 mg of a mixture containing (2'R,3'S)-2'7-(bis)-O-triethylsilyl-9-desoxy-9β-acetoxy-10-desacetoxy-10-keto baccatin (III) and a small amount of the (2'S,3'R) isomer.

To a solution of 42.1 mg (0.045 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 31.2 mg of material which was purified by recrystallization with ether/hexane to give 24.2 mg (57%) of 3'-desphenyl-3'-(2-furyl)-N-desbenzoyl-N-(t-butoxycarbonyl)-7-O-acetyl-10-desacetyl taxol.

m.p.148–150.5° C.; $[\alpha]^{25}_{Na}$−56.9° (c 0.0024, CHCl$_3$).

$^1$H NMR (CDCl$_3$, 300 MHz) δ 8.11(d, J=7.3 Hz, 2H, benzoate ortho), 7.61(m, 1H, benzoate para), 7.50(m, 2H, benzoate meta), 7.42(m, 1H, furyl), 6.38(m, 1H, furyl), 6.33(m, 1H, furyl), 6.23(dd, J=8.2, 0.9 Hz, 1H, H13), 5.69(d, J=6.9 Hz, 1H, H2), 5.48(dd, J=10.5, 7.3 Hz, 1H, H3'), 5.35(d, J=8.7 Hz, H7), 5.33(s, 1H, H10), 5.24(d, J=9.2 Hz, 1H, NH), 4.93 (dd, J=9.6, 1.8 Hz, 1H, H5), 4.71(s, 1H, H2'), 4.33(d, J=8.7 Hz, 1H, H20α), 4.21(d, J=8.7 Hz, 1H, H20β), 4.02(d, J=6.9, 1H, H3), 3.98(d, J=1.8 Hz, 1H, 10 OH), 3.29(d, J=5.5 Hz, 1H, 2'OH), 2.53(m, 1H, H6α), 2.41(s, 3H, 4Ac), 2.33(m, 2H, H14α), 2.30(m, 1H, H14β), 1.99(s, 3H, 7 Ac), 1.96(br s, 3H, Me18), 1.93(m, 1H, H6β), 1.85(s, 3H, Me19), 1.62(s, 1H, 1 OH), 1.36(s, 9H, 3Me t-buthoxy), 1.22(s, 3H, Me17), 1.10(s, 3H, Me16).

EXAMPLE 3

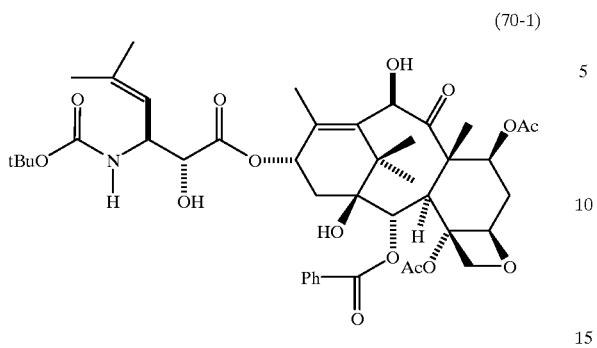

(70-1)

Preparation of 3'-desphenyl-3'-(isobutenyl)-N-desbenzoyl-N-(t-butoxycarbonyl)-7-O-acetyl-10-desacetyl taxol.

To a solution of 7-O-triethylsilyl-9-desoxy-9β-acetoxy-10-desacetoxy-10-keto baccatin (III) (33.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-buthoxycarbonyl-3-(2-methoxyisoropyloxy)-4-isobutenylazetidin-2-one (44.1 mg, 0.141 mmol) in 0.5 mL of THF was added dropwise to the mixture. The solution was warmed to 0° C. and kept at that temperature for 1 h before 1 mL of a 10% solution of ACOH in THF was added. The mixture was partitioned between saturated aqueous NaHCO$_3$ and 60/40 ethyl acetate/hexane. Evaporation of the organic layer gave a residue which was purified by filtration through silica gel to give 41.9 mg of a mixture containing (2'R,3'S)-2'-O-(2-methoxyisopropyl)-7-O-triethylsilyl-3'-desphenyl-3'-(isobutenyl)-N-desbenzoyl-N-(t-butoxycarbonyl)-9-desoxy-9β-acetoxy-10-desacetoxy-10-keto taxol and a small amount of the (2'S,3'R) isomer.

To a solution of 41.9 mg (0.045 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.4 mg of material which was stirred with 1.0 g of silica gel in 5 mL of methylene chloride at room temperature in 48 hrs. The organic layer was purified by filtration through silica gel to give 26.2 mg (70%) of 3'-desphenyl-3'-(isobutenyl)-N-desbenzoyl-N-(t-butoxycarbonyl)-7-O-acetyl-10-desacetyl taxol.

m.p.1136–139° C.; $[\alpha]^{25}_{Na}$ −60.2° (c 0.0025, CHCl$_3$).

$^1$H NMR (CDCl$_3$, 300 MHz) δ 8.10(d, J=7.3 Hz, 2H, benzoate ortho), 7.61(m, 1H, benzoate para), 7.48(m, 2H, benzoate meta), 6.16(td, J=8.7, 1.8 Hz, 1H, H13), 5.68(d, J=6.9 Hz, 1H, H2), 5.48(dd, J=10.5, 7.3 Hz, 1H, H7), 5.33(d, J=1.8 Hz, 1H, H10), 5.32(d, J=9.2 Hz, 1H, NH), 4.94(dd, J=9.6, 1.8 Hz, 1H, H5), 4.80(d, J=8.7 Hz, 1H, Me$_2$C=CH—), 4.75(td, J=8.7, 2.7 Hz, 1H, H3'), 4.33(d, J=8.7 Hz, 1H, H20α), 4.23(d, J=2.7 Hz, 1H, H2'), 4.22(d, J=8.7 Hz, 1H, H20β), 4.01(d, J=6.9 Hz, 1H, H3), 3.98(d, J=1.8 Hz, 1H, 10OH), 3.68(m, 1H, 2'OH), 2.54(m, 1H, H6α), 2.37(s, 3H, 4Ac), 2.35(m, 1H, H14α), 2.01(m, 1H, H14β), 1.99(s, 3H, 7Ac), 1.98(br s, 3H, Me18), 1.93(m, 1H, H6β), 1.85(s, 3H, Me19), 1.77(s, 6H, 2Me from isobuthenyl), 1.61(s, 1H, 7OH), 1.37(s, 9H, 3Me t-buthoxy), 1.23(s, 3H, Me17), 1.10(s, 3H, Me16).

EXAMPLE 4

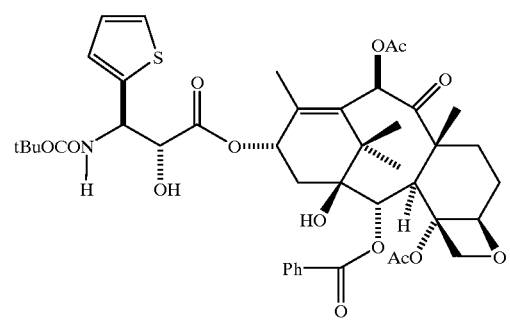

Preparation of 3'-desphenyl-3'-(2-thienyl)-N-desbenzoyl-N-(t-butoxycarbonyl)-7-deshydroxy taxol.

To a solution of 7-deshydroxy baccatin (III) (50.0 mg, 0.082 mmol) in 1.0 mL of THF at −45° C. was added dropwise 0.09 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (94.2 mg, 0.25 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 63.8 mg of a mixture containing (2'R,3'S)-2'-O-triethylsilyl-3'-desphenyl-3'-(2-thienyl)-N-desbenzoyl-N-(t-butoxycarbonyl)-7-deshydroxy taxol and a small amount of the (2'S,3'R) isomer.

To a solution of 63.8 mg (0.067 mmol) of the mixture obtained from the previous reaction in 5.5 mL of acetonitrile and 0.24 mL of pyridine at 0° C. was added 0.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 59.2 mg of material which was purified by flash chromatography to give 54.2 mg (96%) of 3'-desphenyl-3'-(2-thienyl)-N-desbenzoyl-N-(t-butoxycarbonyl)-7-deshydroxy taxol, which was recrystallized from methanol/water.

m.p.148–151° C.; $[\alpha]^{25}_{Na}$ −50.2° (c 0.0025, CHCl$_3$).

$^1$H NMR (CDCl$_3$, 300 MHz) δ 8.13(d, J=7.1 Hz, 2H, benzoate ortho), 7.60(m, 1H, benzoate para), 7.49(m, 2H, benzoate meta), 7.27(dd, J=5.1, 1.2 Hz, 1H, thienyl), 7.07(d, J=3.3 Hz, 1H, thienyl), 7.01(dd, J=5.1, 3.3 Hz, 1H, thienyl), 6.43(s, 1H, H10), 6.23(dd, J=9.0, 0.9 Hz, 1H, H13), 5.68(d, J=7.2 Hz, 1H, H2), 5.50(d, J=9.6 Hz, 1H, H3'), 5.32(d, J=7.2 Hz, 1H, NH), 4.93(dd, J=9.0, 2.1 Hz, 1H, H5), 4.64(d, J=3.3 Hz, 1H, H2'), 4.33(d, J=9.0 Hz, 1H, H20α), 4.19(d, J=9.0 Hz, 1H, H20β), 3.76(d, J=6.6 Hz, 1H, H3), 3.43(m, 1H, 2'OH), 2.38(s, 3H, 4Ac), 2.34(m, 1H, H14α), 2.31(m, 1H, H14β), 2.28(m, 1H, H6α), 2.08(m, 1H, H7α), 1.95(m, 1H, H6β), 1.86(br s, 3H, Me18), 1.71(s, 3H, Me19), 1.66(s, 1H, 1 OH), 1.57(m, 1H, H7β), 1.30(s, 9H, 3Me t-buthoxy), 1.24(s, 3H, Me16), 1.16(s, 3H, Me17)

EXAMPLE 5

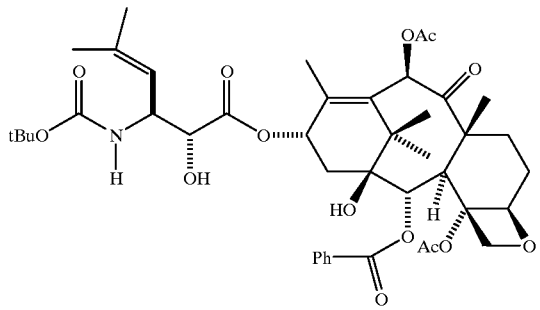

Preparation of 3'-desphenyl-3'-(isobutenyl)-N-desbenzoyl-N-(t-butoxycarbonyl)-7-deshydroxy taxol.

To a solution of 7-deshydroxy baccatin (III) (38.7 mg, 0.063 mmol) in 0.8 mL of THF at −45° C. was added dropwise 0.08 mL of a 0.98 M solution of $LiN(SiMe_3)_2$ in hexane. After 0.5 h at −45° C., a solution of cis-1-t-butoxycarbonyl-3-(2-methoxyisopropyloxy)-4-(isobutenyl) azetidin-2-one (59.0 mg, 0.19 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 43.4 mg of a mixture containing (2'R,3'S)-2'-O-(2-methoxyisopropyl)-3'-desphenyl-3'-(isobutenyl)-N-desbenzoyl-N-(t-butoxycarbonyl)-7-deshydroxy taxol and a small amount of the (2'S,3'R) isomer.

To a solution of 43.4 mg (0.049 mmol) of the mixture obtained from the previous reaction in 3.5 mL of acetonitrile and 0.15 mL of pyridine at 0° C. was added 0.5 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 40.2 mg of material which was purified by flash chromatography to give 34.1 mg (86%) of 3'-desphenyl-3'-(isobutenyl)-N-desbenzoyl-N-(t-butoxycarbonyl)-7-deshydroxy taxol, which was recrystallized from methanol/water.

m.p.142–144° C.; $[\alpha]^{25}_{Na}$−53.3° (c 0.0024, $CHCl_3$).

$^1$H NMR ($CDCl_3$, 300 MHz) δ 8.13(d, J=7.3 Hz, 2H, benzoate ortho), 7.60(m, 1H, benzoate para), 7.47(m, 2H, benzoate meta), 6.41(s, 1H, H10), 6.20(dd, J=9.0, 0.9 Hz, 1H, H13), 5.67(d, J=7.2 Hz, 1H, H2), 5.39(d, J=6.9 Hz, 1H, NH), 5.32(d, J=9.0 Hz, 1H, H3'), 4.93(dd, J=8.7, 2.1 Hz, 1H, H5), 4.81(d, J=8.7 Hz, 1H, $Me_2C=CH—$), 4.61(d, J=3.3 Hz, 1H, H2'), 4.30(d, J=8.1 Hz, 1H, H20α), 4.17(d, J=8.1 Hz, 1H, H20β), 3.75(d, J=6.6 Hz, 1H, H3), 3.41(m, 1H, 2'OH), 2.36(s, 3H, 4Ac), 2.33(m, 1H, H14α), 2.30(m, 1H, H14β), 2.26(m, 1H, H6α), 2.08(m, 1H, H7α), 1.94(m, 1H, H6β), 1.85(br s, 3H, Me18), 1.73(s, 6H, 2Me from isobuthenyl), 1.70(s, 3H, Me19), 1.66(s, 1H, 1 OH), 1.53(m, 1H, H7β), 1.41(s, 9H, 3Me t-buthoxy), 1.25(s, 3H, Me16), 1.15(s, 3H, Me17).

EXAMPLE 6

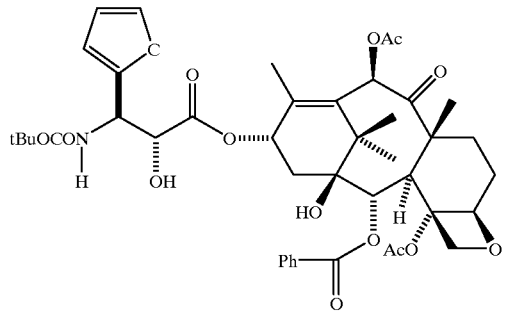

Preparation of 3'-desphenyl-3'-(2-furyl)-N-desbenzoyl-N-(t-butoxycarbonyl)-7-deshydroxy taxol.

To a solution of 7-deshydroxy baccatin (III) (40.0 mg, 0.065 mmol) in 0.8 mL of THF at −45° C. was added dropwise 0.08 mL of a 0.98 M solution of $LiN(SiMe_3)_2$ in hexane. After 0.5 h at −45° C., a solution of cis-1-t-butoxycarbonyl-3-triethylsilyloxy-4-(2-furyl)azetidin-2-one (71.8 mg, 0.20 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 56.0 mg of a mixture containing (2'R,3'S)-2'-O-triethylsilyl-3'-desphenyl-3'-(2-furyl)-N-desbenzoyl-N-(t-butoxycarbonyl)-7-deshydroxy taxol and a small amount of the (2'S,3'R) isomer.

To a solution of 56.0 mg (0.060 mmol) of the mixture obtained from the previous reaction in 4.5 mL of acetonitrile and 0.20 mL of pyridine at 0° C. was added 0.66 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 45.7 mg of material which was purified by flash chromatography to give 37.2 mg (75%) of 3'-desphenyl-3'-(2-furyl)-N-desbenzoyl-N-(t-butoxycarbonyl)-7-deshydroxy taxol, which was recrystallized from methanol/water.

m.p.143–146° C.; $[\alpha]^{25}_{Na}$−56.2° (c 0.0026, $CHCl_3$).

$^1$H NMR ($CDCl_3$, 300 MHz) δ 8.13(d, J=7.1 Hz, 2H, benzoate ortho), 7.61(m, 1H, benzoate para), 7.48(m, 2H, benzoate meta), 7.41(m, 1H, furyl), 6.42(s, 1H, H10), 6.38 (m, 1H, furyl), 6.33(m, 1H, furyl), 6.22(dd, J=9.0, 0.9 Hz, 1H, H13), 5.66(d, J=7.2 Hz, 1H, H2), 5.42(d, J=9.6 Hz, 1H, H3'), 5.27(d, J=7.2 Hz, 1H, NH), 4.92(dd, J=9.0, 2.1 Hz, 1H, H5), 4.61(d, J=3.3 Hz, 1H, H2'), 4.32(d, J=9.0 Hz, 1H, H20α), 4.20(d, J=9.0 Hz, 1H, H20β), 3.77(d, J=6.6 Hz, 1H, H3), 3.41(m, 1H, 2'OH), 2.37(s, 3H, 4Ac), 2.32(m, 1H, H14α), 2.29(m, 1H, H14β), 2.22(m, 1H, H6α), 2.06(m, 1H, H7α), 1.92(m, 1H, H6β), 1.86(br s, 3H, Me18), 1.70(s, 3H, Me19), 1.64(s, 1H, 1 OH), 1.55(m, 1H, H7β), 1.30(s, 9H, 3Me t-buthoxy), 1.25(s, 3H, Me16), 1.16(s, 3H, Me17).

EXAMPLE 7

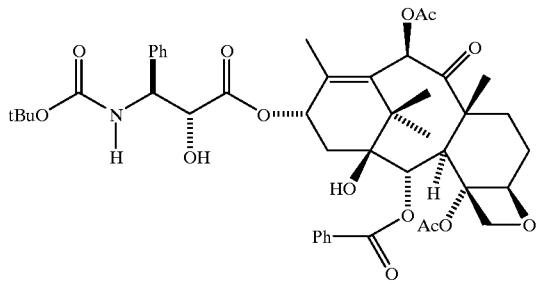

Preparation of N-desbenzoyl-N-(t-butoxycarbonyl)-7-deshydroxy taxol.

To a solution of 7-deshydroxy baccatin (III) (40.0 mg, 0.065 mmol) in 0.8 mL of THF at −45° C. was added dropwise 0.08 mL of a 0.98 M solution of LiN(SiMe$_3$)$_2$ in hexane. After 0.5 h at −45° C., a solution of cis-1-t-butoxycarbonyl-3-triethylsilyloxy-4-(phenyl)azetidin-2-one (73.7 mg, 0.20 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 54.6 mg of a mixture containing (2'R,3'S)-2'-O-triethylsilyl-N-desbenzoyl-N-(t-butoxycarbonyl)-7-deshydroxy taxol and a small amount of the (2'S,3'R) isomer.

To a solution of 54.6 mg (0.055 mmol) of the mixture obtained from the previous reaction in 4.5 mL of acetonitrile and 0.20 mL of pyridine at 0° C. was added 0.66 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 47.7 mg of material which was purified by flash chromatography to give 33.9 mg (74%) of N-desbenzoyl-N-(t-butoxycarbonyl)-7-deshydroxy taxol, which was recrystallized from methanol/water.

m.p.149–152° C; $[\alpha]^{25}_{Na}$ −51.3° (c 0.0025, CHCl$_3$).

$^1$H NMR (CDCl$_3$, 300 MHz) δ 8.13(d, J=7.1 Hz, 2H, benzoate ortho), 7.61(m, 1H, benzoate para), 7.50(m, 2H, benzoate meta), 7.43–7.29(m, 5H, phenyl), 6.45(s, 1H, H10), 6.25(dd, J=9.3, 0.9 Hz, 1H, H13), 5.66(d, J=7.2 Hz, 1H, H2), 5.38(d, J=9.9 Hz, 1H, H3'), 5.26(d, J=7.5 Hz, 1H, NH), 4.93(dd, J=9.0, 2.1 Hz, 1H, H5), 4.61(br s, 1H, H2'), 4.36(d, J=9.0 Hz, 1H, H20α), 4.20(d, J=9.0 Hz, 1H, H20β), 3.76(d, J=6.6 Hz, 1H, H3), 3.32(m, 1H, 2'OH), 2.37(s, 3H, 4Ac), 2.34(m, 1H, H14α), 2.32 (m, 1H, H14β), 2.28 (m, 1H, H6α), 2.05 (m, 1H, H7α), 1.94(m, 1H, H6β), 1.84(br s, 3H, Me18), 1.73(s, 3H, Me19), 1.65(s, 1H, 1 OH), 1.56(m, 1H, H7β),1.31(s, 9H, 3Me t-buthoxy), 1.23(s, 3H, Me16), 1.15 (s, 3H, Me17).

EXAMPLE 8

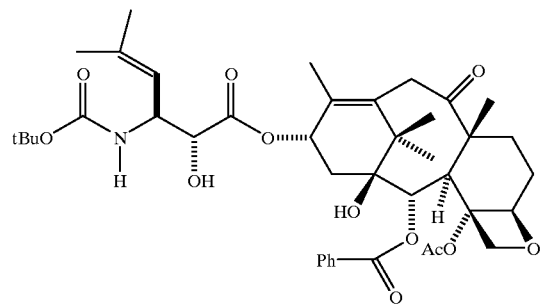

Preparation of 3'-desphenyl-3'-(isobutenyl)-N-desbenzoyl-N-(t-butoxycarbonyl)-7-deshydroxy-10-desacetoxy taxol.

To a solution of 7-deshydroxy-10-desacetoxy baccatin (III) (28.7 mg, 0.051 mmol) in 0.7 mL of THF at −45° C. was added dropwise 0.06 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl)azetidin-2-one (47.3 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.3 mg of a mixture containing (2'R,3'S)-2'-O-(2-methoxyisopropyl)-3'-desphenyl-3'-(isobutenyl)-N-debenzoyl-N-(t-butoxycarbonyl)-7-deshydroxy-10-desacetoxy taxol and a small amount of the (2'S,3'R) isomer.

To a solution of 40.3 mg (0.046 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 35.2 mg of material which was purified by flash chromatography to give 24.0 mg (70%) of 3'-desphenyl-3'-(isobutenyl)-N-debenzoyl-N-(t-butoxycarbonyl)-7-deshydroxy-10-desacetoxy taxol, which was recrystallized from methanol/water.

m.p.122–125° C.; $[\alpha]^{25}_{Na}$ −64.3° (c 0.0025, CHCl$_3$).

$^1$H NMR (CDCl$_3$, 300 MHz) δ 8.12(d, J=7.1 Hz, 2H, benzoate ortho), 7.60(m, 1H, benzoate para), 7.48(m, 2H, benzoate meta), 6.11(td, J=8.1, 1.8 Hz, 1H, H13), 5.68(d, J=6.9 Hz, 1H, H2), 5.23(d, J=9.9 Hz, 1H, NH), 5.12(d, J=9.9 Hz, 1H, H3'), 4.96(dd, J=9.1, 2.7 Hz, 1H, H5), 4.80(d, J=8.7 Hz, 1H, Me$_2$C=CH—), 4.58(dd, J=5.7, 2.1 Hz, 1H, H2'), 4.30(d, J=8.1, 1H, H20α), 4.19(d, J=8.1 Hz, 1H, H20β), 3.97(d, J=6.9 Hz, H3), 3.83(d, J=16.5, 1H, H10α), 3.33(m, 1H, H10β), 3.30(m, 1H, 2'OH), 2.39(m, 1H, H14α), 2.35(s, 3H, 4Ac), 2.26(m, 1H, H14β), 2.19(m, 1H, H6α), 2.10(m, 1H, H7α), 1.95(m, 1H, H6β), 1.73(s, 3H, Me18), 1.69(s, 6H, 2Me from isobuthenyl), 1.63(s, 3H, Me19), 1.44(m, 1H, H7β), 1.39(br. s, 1H, 1 OH), 1.35(s, 9H, 3Me t-buthoxy), 1.25(s, 3H, Me16), 1.15(s, 3H, Me17).

EXAMPLE 9

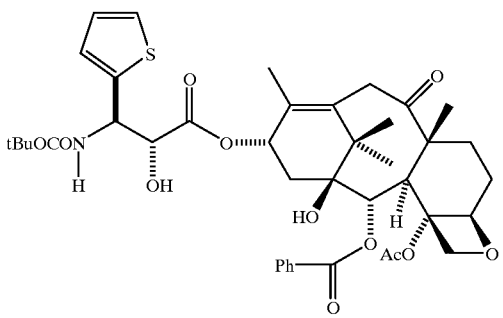

Preparation of 3'-desphenyl-3'-(2-thienyl)-N-desbenzoyl-N-(t-butoxycarbonyl)-7-deshydroxy-10-desacetoxy taxol.

To a solution of 7-deshydroxy-10-desacetoxy baccatin (III) (25.0 mg, 0.044 mmol) in 0.7 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)-azetidin-2-one (50.0 mg, 0.13 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 35.4 mg of a mixture containing (2'R,3'S)-2'-O-triethylsilyl-3'-desphenyl-3'-(2-thienyl)-N-desbenzoyl-N-(t-butoxycarbonyl)-7-deshydroxy-10-desacetoxy taxol and a small amount of the (2'S,3'R) isomer.

To a solution of 35.4 mg (0.037 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.4 mg of material which was purified by flash chromatography to give 20.5 mg (71%) of 3'-desphenyl-3'-(2-thienyl)-N-desbenzoyl-N-(t-butoxycarbonyl)-7-deshydroxy-10-desacetoxy taxol, which was recrystallized from methanol/water.

m.p.132–134° C.; $[\alpha]^{25}_{Na}$−61.3° (c 0.0025, CHCl$_3$).

$^1$H NMR (CDCl$_3$, 300 MHz) δ 8.14(d, J=7.1 Hz, 2H, benzoate ortho), 7.61(m, 1H, benzoate para), 7.51(m, 2H, benzoate meta), 7.29(dd, J=5.4, 1.2 Hz, 1H, thienyl), 7.09(d, J=3.3 Hz, 1H, thienyl), 7.01(dd, J=5.4, 3.3 Hz, 1H, thienyl), 6.14(td, J=8.4, 1.8 Hz, 1H, H13), 5.69(d, J=6.9 Hz, 1H, H2), 5.24(d, J=9.9 Hz, 1H, NH), 5.19(d, J=9.9 Hz, 1H, H3'), 4.93(dd, J=9.3, 2.7 Hz, 1H, H5), 4.62(dd, J=5.7, 2.1 Hz, 1H, H2'), 4.31(d, J=8.1, 1H, H20α), 4.21(d, J=8.1 Hz, 1H, H20β), 3.98(d, J=6.9 Hz, H3), 3.84(d, J=16.5, 1H, H10α), 3.38(m, 1H, H10β), 3.33(m, 1H, 2'OH), 2.40(m, 1H, H14α), 2.37(s, 3H, 4Ac), 2.27(m, 1H, H14β), 2.20(m, 1H, H6α), 2.11(m, 1H, H7α), 1.95(m, 1H, H6β), 1.74(s, 3H, Me18), 1.71(s, 3H, Me19), 1.46(m, 1H, H7β), 1.40(br. s, 1H, 1 OH), 1.34(s, 9H, 3Me t-buthoxy), 1.24(s, 3H, Me16), 1.13(s, 3H, Me17).

EXAMPLE 10

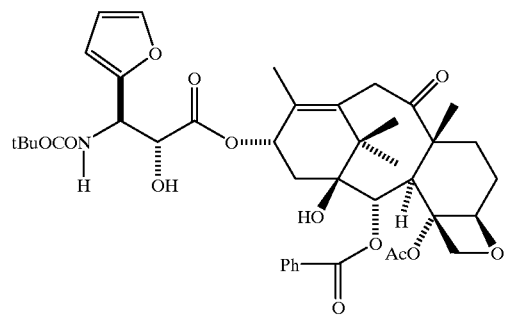

Preparation of 3'-desphenyl-3'-(2-furyl)-N-desbenzoyl-N-(t-butoxycarbonyl)-7-deshydroxy-10-desacetoxy taxol.

To a solution of 7-deshydroxy-10-desacetoxy baccatin (III) (35.0 mg, 0.061 mmol) in 0.8 mL of THF at −45° C. was added dropwise 0.07 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)-azetidin-2-one (68.0 mg, 0.18 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 56.3 mg of a mixture containing (2'R,3'S)-2'-O-triethylsilyl-3'-desphenyl-3'-(2-furyl)-N-desbenzoyl-N-(t-butoxycarbonyl)-7-deshydroxy-10-desacetoxy taxol and a small amount of the (2'S,3'R) isomer.

To a solution of 56.3 mg (0.06 mmol) of the mixture obtained from the previous reaction in 4.6 mL of acetonitrile and 0.22 mL of pyridine at 0° C. was added 0.68 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 48.3 mg of material which was purified by flash chromatography to give 31.7 mg (69%) of 3'-desphenyl-3'-(2-furyl)-N-desbenzoyl-N-(t-butoxycarbonyl)-7-deshydroxy-10-desacetoxy taxol, which was recrystallized from methanol/water.

m.p.128–131° C.; $[\alpha]^{25}_{Na}$−66.9° (c 0.0028, CHCl$_3$).

$^1$H NMR (CDCl$_3$, 300 MHz) δ 8.13(d, J=6.9 Hz, 2H, benzoate ortho), 7.60(m, 1H, benzoate para), 7.48(m, 2H, benzoate meta), 7.40(m, 1H, furyl), 6.38(m, 1H, furyl), 6.32(m, 1H, furyl), 6.12(td, J=8.1, 1.8 Hz, 1H, H13), 5.67(d, J=6.9 Hz, 1H, H2), 5.22(d, J=9.9 Hz, 1H, NH), 5.17(d, J=9.9 Hz, 1H, H3'), 4.91(dd, J=9.1, 2.7 Hz, 1H, H5), 4.60(dd, J=5.7, 2.1 Hz, 1H, H2'), 4.28(d, J=8.1, 1H, H20α), 4.21(d, J=8.1 Hz, 1H, H20β), 3.95(d, J=6.9 Hz, H3), 3.82(d, J=16.5, 1H, H10α), 3.33(m, 1H, H10β), 3.31(m, 1H, 2'OH), 2.38(m, 1H, H14α), 2.35(s, 3H, 4Ac), 2.23(m, 1H, H14β), 2.20(m, 1H, H6α), 2.11(m, 1H, H7α), 1.94(m, 1H, H6β), 1.73(s, 3H, Me18), 1.71(s, 3H, Me19), 1.43(m, 1H, H7β), 1.38(br. s, 1H, 1 OH), 1.32(s, 9H, 3Me t-buthoxy), 1.23(s, 3H, Me16), 1.12(s, 3H, Me17).

EXAMPLE 11

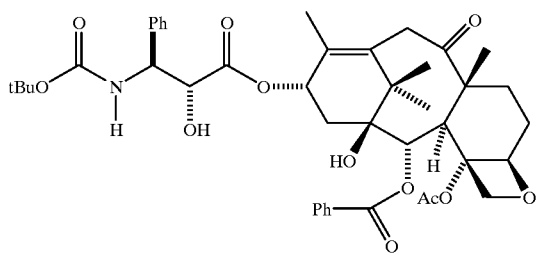

Preparation of N-desbenzoyl-N-(t-butoxycarbonyl)-7-deshydroxy-10-desacetoxy taxol.

To a solution of 7-deshydroxy-10-desacetoxy baccatin (III) (28.0 mg, 0.049 mmol) in 0.7 mL of THF at −45° C. was added dropwise 0.06 mL of a 0.98 M solution of LiN(SiMe$_3$)$_2$ in hexane. After 0.5 h at −45° C., a solution of cis-1-t-butoxycarbonyl-3-triethylsilyloxy-4-(phenyl) azetidin-2-one (56.0 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 38.4 mg of a mixture containing (2'R,3'S)-2'-O-triethylsilyl-N-desbenzoyl-N-(t-butoxycarbonyl)-7-deshydroxy-10-desacetoxy taxol and a small amount of the (2'S,3'R) isomer.

To a solution of 38.4 mg (0.041 mmol) of the mixture obtained from the previous reaction in 3.2 mL of acetonitrile and 0.15 mL of pyridine at 0° C. was added 0.46 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.8 mg of material which was purified by flash chromatography to give 27.4 mg (71%) of N-desbenzoyl-N-(t-butoxycarbonyl)-7-deshydroxy-10-desacetoxy taxol, which was recrystallized from methanol/water.

m.p.135–138° C.; $[\alpha]^{25}_{Na}$ −65.2° (c 0.0025, CHCl$_3$).

1H NMR (CDCl$_3$, 300 MHz) δ 8.12(d, J=7.1 Hz, 2H, benzoate ortho), 7.60(m, 1H, benzoate para), 7.51(m, 2H, benzoate meta), 7.42–7.29(m, 5H, phenyl), 6.12(td, J=8.1, 1.8 Hz, 1H, H13), 5.66(d, J=6.9 Hz, 1H, H2), 5.21(d, J=9.9 Hz, 1H, NH), 5.16(d, J=9.9 Hz, 1H, H3'), 4.92(dd, J=9.1, 2.7 Hz, 1H, H5), 4.58(dd, J=5.7, 2.1 Hz, 1H, H2'), 4.30(d, J=8.1, 1H, H20α), 4.21(d, J=8.1 Hz, 1H, H20β), 3.97(d, J=6.9 Hz, H3), 3.82 (d, J=16.5, 1H, H10α), 3.41(m, 1H, H10β), 3.36(m, 1H, 2'OH), 2.40(m, 1H, H14α), 2.38(s, 3H, 4Ac), 2.26(m, 1H, H14β), 2.20(m, 1H, H6α), 2.13(m, 1H, H7α), 1.93(m, 1H, H6β), 1.73(s, 3H, Me18), 1.70(s, 3H, Me19), 1.43(m, 1H, H7β), 1.38(br. s, 1H, 1 OH), 1.32(s, 9H, 3Me t-buthoxy), 1.25(s, 3H, Me16), 1.15(s, 3H, Me17)

EXAMPLE 12

The taxanes of the prior examples were evaluated in in vitro cytotoxicity activity against human colon carcinoma cells HCT-116. Cytotoxicity was assessed in HCT116 and human colon carcinoma cells by XTT (2,3-bis(2-methoxy-4-nitro-5-sulfophenyl)-5-[(phenylamino)carbonyl]-2H-tetrazolium hydroxide) assay (Scudiero et al, "Evaluation of a soluble tetrazolium/formazan assay for cell growth and drug sensitivity in culture using human and other tumor cell lines", *Cancer Res.* 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC$_{50}$ which is the drug concentration required to inhibit cell proliferation (i.e. absorbance at 450 nm) to 50% of that of untreated control cells.

All compounds had an IC$_{50}$ less than 0.1, indicating that they were all cytotoxically active.

What I claim is:

1. A taxane having the formula

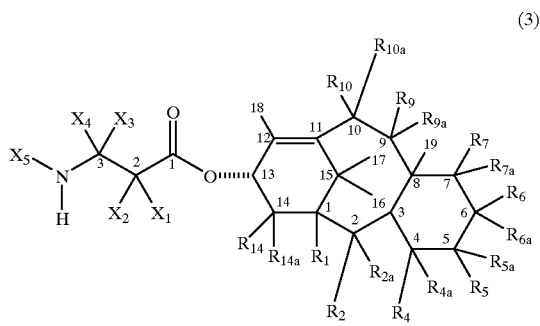

(3)

wherein $X_1$ is —OX$_6$, —SX$_7$, or —NX$_8$X$_9$;

$X_2$ is hydrogen, or substituted or unsubstituted alkyl, alkenyl, alkynyl, aryl, or heteroaryl;

$X_3$ and $X_4$ are independently hydrogen, or substituted or unsubstituted alkyl, alkenyl, alkynyl, aryl, or heteroaryl;

$X_5$ is —COX$_{10}$, —COOX$_{10}$, —COSX$_{10}$, —CONX$_8$X$_{10}$, or —SO$_2$X$_{11}$;

$X_6$ is hydrogen, or substituted or unsubstituted alkyl, alkenyl, alkynyl, aryl, or heteroaryl, or hydroxy protecting group, or a functional group which increases the water solubility of the taxane derivative;

$X_7$ is substituted or unsubstituted alkyl, alkenyl, alkynyl, aryl, or heteroaryl, or sulfhydryl protecting group;

$X_8$ is hydrogen, or substituted or unsubstituted alkyl, alkenyl, alkynyl, aryl, or heteroaryl, or heterosubstituted alkyl, alkenyl, alkynyl, aryl or heteroaryl;

$X_9$ is an amino protecting group;

$X_{10}$ is or substituted or unsubstituted alkyl, alkenyl, alkynyl, aryl, or heteroaryl, or heterosubstituted alkyl, alkenyl alkynyl, aryl or heteroaryl;

$X_{11}$ is substituted or unsubstituted alkyl, alkenyl, alkynyl, aryl, or heteroaryl, —OX$_{10}$, or —NX$_8$X$_{14}$;

$X_{14}$ is hydrogen, or substituted or unsubstituted alkyl, alkenyl, alkynyl, aryl, or heteroaryl;

$R_1$ is hydrogen, hydroxy, protected hydroxy or together with $R_{14}$ forms a carbonate;

$R_2$ is hydrogen, hydroxy, —OCOR$_{31}$, or together with $R_{2a}$ forms an oxo;

$R_{2a}$ is hydrogen or together with $R_2$ forms an oxo;

$R_4$ is hydrogen, or together with $R_{4a}$ forms an oxo, oxirane or methylene;

$R_{4a}$ is hydrogen, or substituted or unsubstituted alkyl, alkenyl, alkynyl, aryl, or heteroaryl, or cyano, hydroxy, —OCOR$_{30}$, or together with R$_4$ forms an oxo, oxirane or methylene;

R$_5$ is hydrogen or together with R$_{5a}$ forms an oxo;

R$_{5a}$ is hydrogen, hydroxy, protected hydroxy, acyloxy, or together with R$_5$ forms an oxo;

R$_6$ is hydrogen, or substituted or unsubstituted alkyl, alkenyl, alkynyl, aryl, or heteroaryl, or hydroxy, protected hydroxy or together with R$_{6a}$ forms an oxo;

R$_{6a}$ is hydrogen, or substituted or unsubstituted alkyl, alkenyl, alkynyl, aryl, or heteroaryl, or hydroxy, protected hydroxy or together with R$_6$ forms an oxo;

R$_7$ is hydrogen or acyloxy;

R$_{7a}$ is hydrogen;

R$_9$ is hydrogen or together with R$_{9a}$ forms an oxo;

R$_{9a}$ is hydrogen, hydroxy, protected hydroxy, acyloxy, or together with R$_9$ forms an oxo;

R$_{10}$ is hydrogen or together with R$_{10a}$ forms an oxo;

R$_{10a}$ is hydrogen, —OCOR$_{29}$, hydroxy, or protected hydroxy, or together with R$_{10}$ forms an oxo;

R$_{14}$ is hydrogen, or substituted or unsubstituted alkyl, alkenyl, alkynyl, aryl, or heteroaryl, or hydroxy, protected hydroxy or together with R$_1$ forms a carbonate;

R$_{14a}$ is hydrogen, or substituted or unsubstituted alkyl, alkenyl, alkynyl, aryl, or heteroaryl; and R$_{29}$, R$_{30}$ and R$_{31}$ are independently hydrogen, or substituted or unsubstituted alkyl, alkenyl, alkynyl, monocyclic aryl or monocyclic heteroaryl.

2. The taxane of claim 1 wherein R$_{7a}$ and R$_7$ are hydrogen.

3. The taxane of claim 1 wherein R$_{7a}$ is hydrogen and R$_7$ is acetoxy.

4. A pharmaceutical composition which contains the taxane of claim 1 and one or more pharmacologically acceptable, inert or physiologically active diluents or adjuvants.

5. The taxane of claim 1 wherein R$_1$ is hydroxy.

6. The taxane of claim 1 wherein R$_2$ is benzoyloxy, and R$_{2a}$ is hydrogen.

7. The taxane of claim 1 wherein R$_{4a}$ is acetoxy.

8. The taxane of claim 1 wherein R$_6$ and R$_{6a}$ are hydrogen.

9. The taxane of claim 1 wherein R$_{9a}$ together with R$_9$ forms an oxo.

10. The taxane of claim 1 wherein R$_{10}$ is hydrogen; and R$_{10a}$ is acetoxy, hydroxy, or protected hydroxy.

11. The taxane of claim 1 wherein R$_{14}$ and R$_{14a}$ are hydrogen.

12. The taxane of claim 1 wherein X$_1$ is —OX$_6$; X$_2$ is hydrogen or alkyl; X$_3$ is substituted or unsubstituted alkyl, alkenyl, alkynyl, aryl or heteroaryl; X$_4$ is hydrogen; and X$_6$ is hydrogen or hydroxy protecting group.

13. The taxane of claim 1 wherein

R$_1$ is hydroxy;

R$_{2a}$ is hydrogen, and R$_2$ is —OCOR$_{31}$;

R$_{4a}$ is —OCOR$_{30}$;

R$_6$ and R$_{6a}$ are hydrogen;

R$_{9a}$ together with R$_9$ forms an oxo;

R$_{10}$ is hydrogen, and R$_{10a}$ is —OCOR$_{29}$, hydroxy, or protected hydroxy;

R$_{14}$ and R$_{14a}$ are hydrogen;

R$_{29}$ and R$_{30}$ are independently substituted or unsubstituted alkyl; and

R$_{31}$ is substituted or unsubstituted monocyclic aryl.

14. The taxane of claim 12 wherein

R$_1$ is hydroxy;

R$_{2a}$ is hydrogen, and R$_2$ is —OCOR$_{31}$;

R$_{4a}$ is —OCOR$_{30}$;

R$_6$ and R$_{6a}$ are hydrogen;

R$_{9a}$ together with R$_9$ forms an oxo;

R$_{10}$ is hydrogen, and R$_{10a}$ is —OCOR$_{29}$, hydroxy, or protected hydroxy;

R$_{14}$ and R$_{14a}$ are hydrogen;

R$_{29}$ and R$_{30}$ are independently substituted or unsubstituted alkyl; and

R$_{31}$ is substituted or unsubstituted monocyclic aryl.

15. The taxane of claim 14 wherein R$_2$ is benzoyloxy.

16. The taxane of claim 14 wherein R$_{4a}$ and R$_{29}$ are acetoxy.

17. The taxane of claim 1 wherein X$_5$ is benzoyl or t-butoxycarbonyl.

18. The taxane of claim 1 wherein R$_1$ is hydrogen, or together with R$_{14}$ forms a carbonate.

19. The taxane of claim 1 wherein R$_{31}$ is hydrogen, or substituted or unsubstituted alkyl, alkenyl, alkynyl, or monocyclic heteroaryl.

20. The taxane of claim 1 wherein R$_{30}$ is hydrogen, or substituted or unsubstituted alkenyl, alkynyl, monocyclic aryl or monocyclic heteroaryl.

21. The taxane of claim 1 wherein R$_9$ is hydrogen, and R$_{9a}$ is hydrogen, hydroxy, protected hydroxy, or acyloxy.

22. The taxane of claim 1 wherein R$_{10}$ is hydrogen or together with R$_{10a}$ forms an oxo; and R$_{10a}$ is hydrogen or together with R$_{10}$ forms an oxo.

23. The taxane of claim 1 wherein R$_{14}$ is substituted or unsubstituted alkyl, alkenyl, alkynyl, aryl, or heteroaryl, hydroxy, protected hydroxy or together with R$_1$ forms a carbonate.

24. A taxane having the formula (3)

wherein

X$_1$ is —OX$_6$, —SX$_7$, or —NX$_8$X$_9$;

X$_2$ is hydrogen, or substituted or unsubstituted alkyl, alkenyl, alkynyl, aryl, or heteroaryl;

X$_3$ and X$_4$ are independently hydrogen, or substituted or unsubstituted alkyl, alkenyl, alkynyl, aryl, or heteroaryl;

X$_5$ is —COX$_{10}$, —COOX$_{10}$, —COSX$_{10}$, —CONX$_8$X$_{10}$, or —SO$_2$X$_{11}$;

X$_6$ is hydrogen, or substituted or unsubstituted alkyl, alkenyl, alkynyl, aryl, or heteroaryl, or hydroxy protecting group;

X$_7$ is substituted or unsubstituted alkyl, alkenyl, alkynyl, aryl, or heteroaryl, or sulfhydryl protecting group;

X$_8$ is hydrogen, or substituted or unsubstituted alkyl, alkenyl, alkynyl, aryl, or heteroaryl;

$X_9$ is an amino protecting group;

$X_{10}$ is substituted or unsubstituted alkyl, alkenyl, alkynyl, aryl, or heteroaryl;

$X_{11}$ is substituted or unsubstituted alkyl, alkenyl, alkynyl, aryl, or heteroaryl, or —$OX_{10}$, or —$NX_8X_{14}$;

$X_{14}$ is hydrogen, or substituted or unsubstituted alkyl, alkenyl, alkynyl, aryl, or heteroaryl;

$R_1$ is hydroxy, protected hydroxy or together with $R_{14}$ forms a carbonate;

$R_2$ is hydrogen, hydroxy, or —$OCOR_{31}$;

$R_{2a}$ is hydrogen;

$R_4$ is hydrogen, or together with $R_{4a}$ forms an oxo, oxirane or methylene;

$R_{4a}$ is hydrogen, or substituted or unsubstituted alkyl, alkenyl, alkynyl, aryl, or heteroaryl, or cyano, hydroxy, —$OCOR_{30}$, or together with $R_4$ forms an oxo, oxirane or methylene;

$R_5$ is hydrogen or together with $R_{5a}$ forms an oxo;

$R_{5a}$ is hydrogen, hydroxy, protected hydroxy, acyloxy, or together with $R_5$ forms an oxo;

$R_6$ and $R_{6a}$ are hydrogen;

$R_7$ is hydrogen or acyloxy;

$R_{7a}$ is hydrogen;

$R_9$ is hydrogen or together with $R_{9a}$ forms an oxo;

$R_{9a}$ is hydrogen, hydroxy, protected hydroxy, acyloxy, or together with $R_9$ forms an oxo;

$R_{10}$ is hydrogen or together with $R_{10a}$ forms an oxo, $R_{10a}$ is hydrogen, —$OCOR_{29}$, hydroxy, or protected hydroxy, or together with $R_{10}$ forms an oxo;

$R_{14}$ is hydrogen, hydroxy, protected hydroxy or together with $R_1$ forms a carbonate;

$R_{14a}$ is hydrogen; and $R_{29}$, $R_{30}$ and $R_{31}$ are independently hydrogen, or substituted or unsubstituted alkyl, alkenyl, alkynyl, monocyclic aryl or monocyclic heteroaryl.

25. The taxane of claim 24 wherein $R_{7a}$ and $R_7$ are hydrogen.

26. The taxane of claim 24 wherein $R_{7a}$ is hydrogen and $R_7$ is acetoxy.

27. The taxane of claim 1 wherein:

$R_4$ is hydrogen, or together with $R_{4a}$ forms an oxo, oxirane or methylene;

$R_{4a}$ is hydrogen, hydroxy, alkyl, or together with $R_4$ forms an oxo, oxirane or methylene;

$R_5$ is hydrogen;

$R_{5a}$ is hydrogen, hydroxy, protected hydroxy or acyloxy; and $R_{30}$ is as defined in claim 1.

28. The taxane of claim 24 wherein:

$R_4$ is hydrogen, or together with $R_{4a}$ forms an oxo, oxirane or methylene;

$R_{4a}$ is hydrogen, hydroxy, alkyl, or together with $R_4$ forms an oxo, oxirane or methylene;

$R_5$ is hydrogen;

$R_{5a}$ is hydrogen, hydroxy, protected hydroxy or acyloxy; and $R_{30}$ is as defined in claim 24.

* * * * *

UNITED STATES PATENT AND TRADEMARK OFFICE
CERTIFICATE OF CORRECTION

PATENT NO. : 5,994,576
DATED : November 30, 1999
INVENTOR(S) : Robert A. Holton and Ki-byung Chai It is certified that error appears in the above-identified patent and that said Letters Patent is hereby corrected as shown below:

Column 1,
Lines 35-43, chemical structure (1) should read

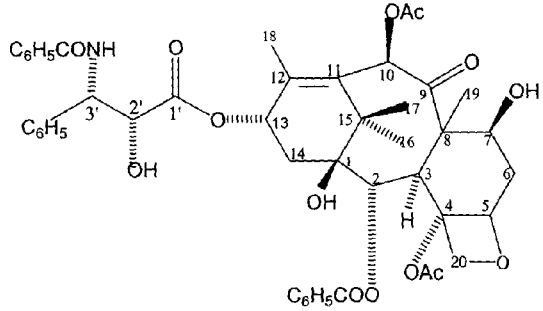

Lines 54-63, chemical structure (2) should read

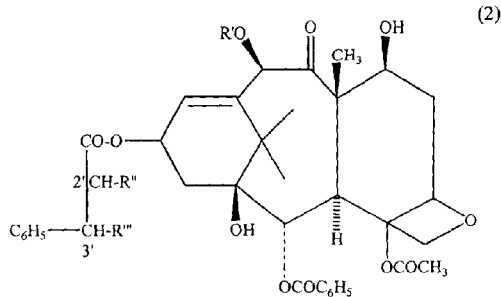

Line 4, "hydrogen R" is" should read -- hydrogen, R" is --.

Column 2,
Lines 22-32, chemical structure (3) should read

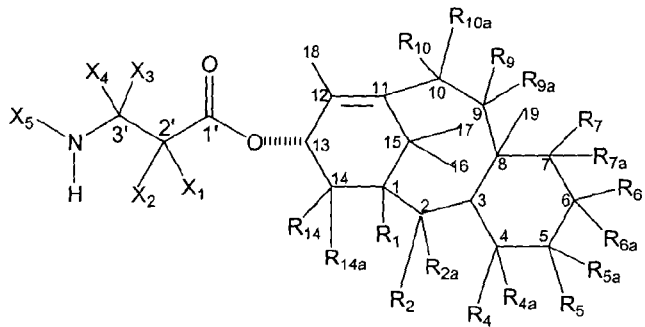

UNITED STATES PATENT AND TRADEMARK OFFICE
CERTIFICATE OF CORRECTION

PATENT NO. : 5,994,576
DATED : November 30, 1999
INVENTOR(S) : Robert A. Holton and Ki-byung Chai It is certified that error appears in the above-identified patent and that said Letters Patent is hereby corrected as shown below:

Columns 5 and 6,
Scheme A, the first recited structure should read

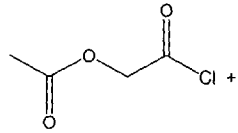

Column 8,
Lines 35-43, the chemical structure should read

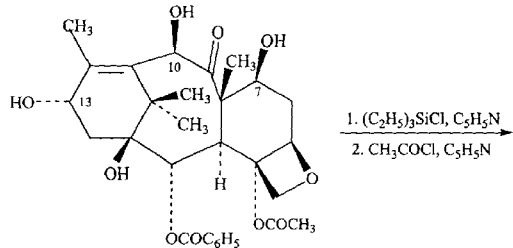

Lines 43-52, the chemical structure should read

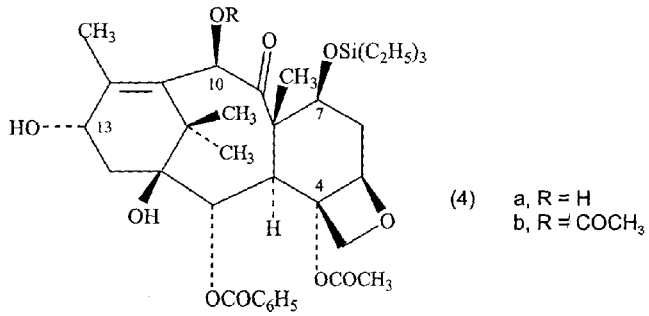

UNITED STATES PATENT AND TRADEMARK OFFICE
CERTIFICATE OF CORRECTION

PATENT NO. : 5,994,576
DATED : November 30, 1999
INVENTOR(S) : Robert A. Holton and Ki-byung Chai It is certified that error appears in the above-identified patent and that said Letters Patent is hereby corrected as shown below:

Column 9,
Lines 34-46, the chemical structures should read

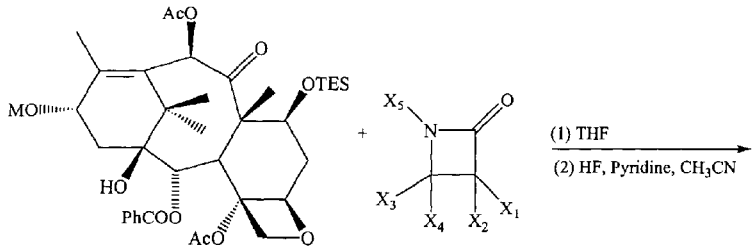

Column 11,
Line 33, that portion reading "TESCi" should read -- TESCl --.

Column 18,
Line 44, "Triol 18" should start a new paragraph.
Lines 57-66, chemical structure 18 should read

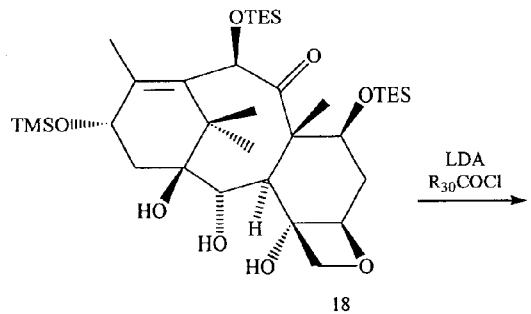

Column 22,
Scheme 10, line 14, that portion reading "1) TESCI, py" should read
-- 1) TESCl, py --.
Line 15, that portion reading "2) TMSCI, DMAP" should read
-- 2) TMSCl, DMAP --.

UNITED STATES PATENT AND TRADEMARK OFFICE
CERTIFICATE OF CORRECTION

PATENT NO.    : 5,994,576
DATED         : November 30, 1999
INVENTOR(S)   : Robert A. Holton and Ki-byung Chai It is certified that error appears in the above-identified patent and that said Letters Patent is hereby corrected as shown below:

Column 22, cont'd,
Scheme 10, chemical structure 24 should read

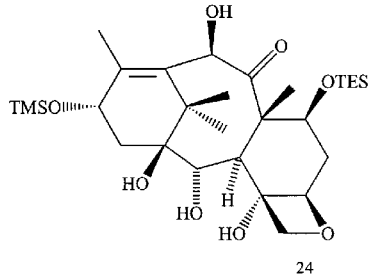

Scheme 10, approximately lines 54-64, the last structure should read

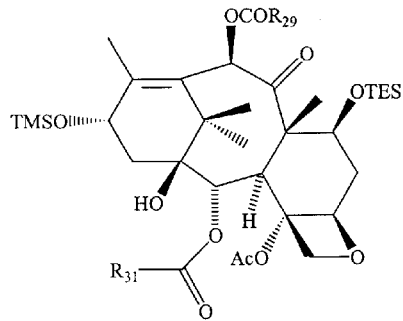

Column 23,
Line 38, that portion reading "rBu$_3$SnH" should read -- nBu$_3$SnH --.

Columns 23 and 24,
Reaction Scheme 12, chemical structure 11 should read

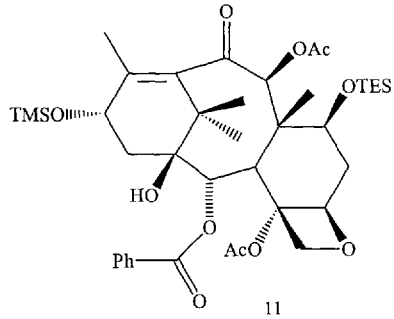

UNITED STATES PATENT AND TRADEMARK OFFICE
CERTIFICATE OF CORRECTION

PATENT NO. : 5,994,576  
DATED : November 30, 1999  
INVENTOR(S) : Robert A. Holton and Ki-byung Chai Page 5 of 6

It is certified that error appears in the above-identified patent and that said Letters Patent is hereby corrected as shown below:

Column 26,  
Lines 12-18, the chemical structure should read

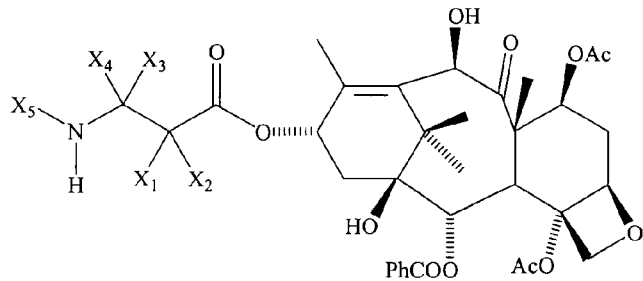

Column 32,  
Lines 2-23, the chemical structure should read

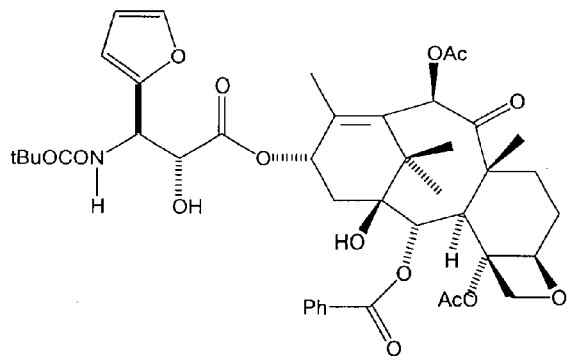

Column 38,  
Lines 17-28, the chemical structure (3) should read

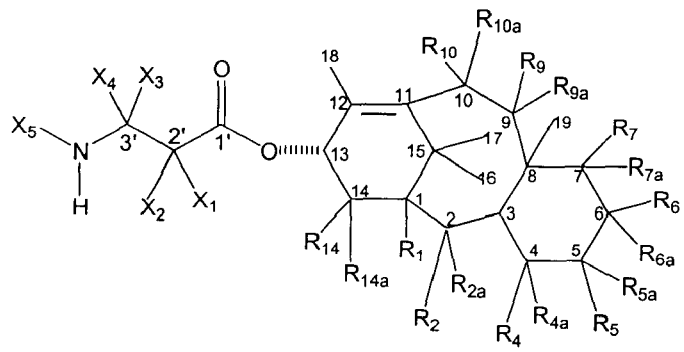

UNITED STATES PATENT AND TRADEMARK OFFICE
CERTIFICATE OF CORRECTION

PATENT NO.    : 5,994,576
DATED         : November 30, 1999
INVENTOR(S)   : Robert A. Holton and Ki-byung Chai It is certified that error appears in the above-identified patent and that said Letters Patent is hereby corrected as shown below:

Column 38, cont'd,
Line 51, "is or substituted" should read -- is substituted --.

Column 39,
Line 21, "$R_{10}$forms" should read -- $R_{10}$ forms --.

Column 40,
Lines 38-48, chemical structure (3) should read

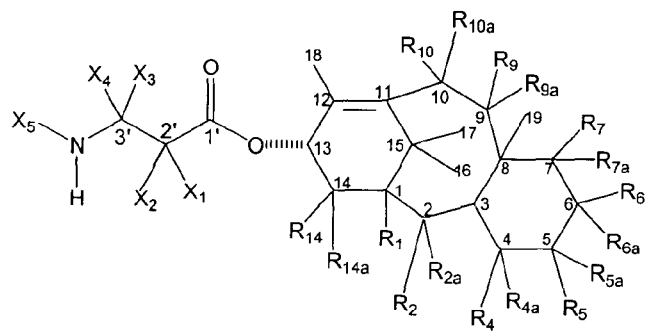

Signed and Sealed this

Twenty-seventh Day of January, 2004

JON W. DUDAS
*Acting Director of the United States Patent and Trademark Office*